US008323665B2

(12) United States Patent
Vitetta et al.

(10) Patent No.: US 8,323,665 B2
(45) Date of Patent: *Dec. 4, 2012

(54) RICIN A CHAIN MUTANTS LACKING ENZYMATIC ACTIVITY AS VACCINES TO PROTECT AGAINST AEROSOLIZED RICIN

(75) Inventors: Ellen S. Vitetta, Dallas, TX (US); Victor F. Ghetie, Dallas, TX (US); Joan E. Smallshaw, Dallas, TX (US); Roxana G. Baluna, San Antonio, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 1605 days.

This patent is subject to a terminal disclaimer.

(21) Appl. No.: 11/673,981

(22) Filed: Feb. 12, 2007

(65) Prior Publication Data

US 2012/0123097 A1    May 17, 2012

Related U.S. Application Data

(60) Division of application No. 09/698,551, filed on Oct. 26, 2000, now Pat. No. 7,175,848, which is a continuation-in-part of application No. 09/668,419, filed on Sep. 22, 2000, now abandoned.

(51) Int. Cl.
*A61K 39/02* (2006.01)
*A61K 36/47* (2006.01)
*A61K 38/56* (2006.01)
*C07K 4/10* (2006.01)

(52) U.S. Cl. ............... 424/236.1; 530/350; 530/370; 530/396; 514/2.1

(58) Field of Classification Search .............. None
See application file for complete search history.

(56) References Cited

U.S. PATENT DOCUMENTS

| | | | | |
|---|---|---|---|---|
| 4,350,626 | A | 9/1982 | Masuho et al. | 530/391.9 |
| 4,372,883 | A | 2/1983 | Matuhashi et al. | 424/197.11 |
| 4,490,362 | A | 12/1984 | Shionoya et al. | 424/278.1 |
| 5,453,271 | A | 9/1995 | Lemley et al. | 424/184.1 |
| 5,578,706 | A | 11/1996 | Ghetie et al. | 530/391.7 |
| 5,932,217 | A | 8/1999 | Tuomanen et al. | 424/185.1 |
| 6,566,500 | B1 * | 5/2003 | Vitetta et al. | 530/350 |
| 7,452,971 | B2 * | 11/2008 | Vitetta et al. | 530/350 |
| 7,829,668 | B2 * | 11/2010 | Vitetta et al. | 530/350 |

OTHER PUBLICATIONS

Kim et al, Biochemistry 31(12): 3294-3296, Mar. 1992.*
Day et al, Biochemistry 35: 11098-11103, 1996.*
Fryxell et al, Protein Science 7: 318-324, 1998.*
Lu et al., "Substitutions of proline 42 alanine and methionine 46 to asparagine around the RGD domain of the neurotoxin dendroaspin alter its preferential antagonism to that resembling the disintegrin elegantin," *J. Biol. Chem.*, 271:289-94, 1996.
Morris and Wool, "Determination by systematic deletion of the amino acids essential for catalysis by ricin A chain," *Proc. Natl. Acad. Sci. USA*, 89:4869-73, 1992.

Abaza and Atassi., "Effects of Amino Acid Substitutions Outisde an Antigenic Site on Protein Binding to Monoclonal Antibodies of Predetermined Specificity Obtained by Peptide Immunization: Demonstration with Region 94-100 (Antigenic Site 3) of Myoglobin," *J. of Protein Chemistry*, 11:433-444, 1992.
Baluna and Vitetta, "An in vivo model to study immunotoxin-induced vascular leak in human tissue," *J. Immunother.*, 22(1):41-47, 1999.
Baluna and Vitetta, "Vascular leak syndrome: A side effect of immunotherapy," *Immunopharmacology*, 37:117-132, 1997.
Baluna et al., "Evidence for a structural motif in toxins and interleukin-2 that may be responsible for binding to endothelial cells and initiating vascular leak syndrome," *Proc Natl Acad Sci U S A.*, 96(7):3957-3962, 1999.
Baluna et al., "The effect of a monoclonal antibody coupled to ricin A chain-derived peptides on endothelial cells in vitro: insights into toxin-mediated vascular damage," *Exp Cell Res.* 258(2):417-424, 2000.
Baluna et al., "Fibronectin inhibits the cytotoxic effect of ricin A chain on endothelial cells," *Int. J. Immunopharm.*, 18:355-361, 1996.
Chaddock and Roberts, "Mutagenesis and kinetic analysis of the active site Glu177 of ricin A-chain," *Protein Eng.*, 6(4):425-431, 1993.
Clements et al., "Identification of a key integrin-binding sequence in VCAM-1 homologous to the LDV active site in fibronectin," *J. Cell Sci.*, 107:2127-2135, 1994.
Engert et al., "The emerging role of ricin A-chain immunotoxins in leukemia and lymphoma," *In: Clinical Applications of Immunotoxins*, Frankel (ed.), 2:13-33, 1997.
Frankel et al., "Role of arginine 180 and glutamic acid 177 of ricin toxin A chain in enzymatic inactivation of ribosomes," *Mol. Cell. Biol.*, 10(12):6257-6263, 1990.
Ghetie et al., "Evaluation of ricin A chain-containing immunotoxins directed against CD19 and CD22 antigens on normal and malignant human B-cells as potential reagents for in vivo therapy," *Cancer Res.* 48:2610-2617, 1988.
Ghetie et al., "The GLP large scale preparation of immunotoxins containing deglycosylated ricin A chain and a hindered disulfide bond," *J. Immunol Methods*, 142(2):223-230, 1991.
Griffiths et al., "Local and systemic responses against ricin toxin promoted by toxoid or peptide vaccines alone or in liposomal formulations," *Vaccine*, 16:530-535, 1998.
Heweston et al., "Protection of mice from inhaled ricin by vaccination with formalized ricin toxoid," *Toxicon*, 31:138-139, 1993.
Hewetson et al. "Protection of mice from inhaled ricin by vaccination with ricin or by passive treatment with heterologous antibody," *Vaccine*, 11(7):743-746, 1993. Abstract attached (Reports and Abstracts 138-139).
Hewetson et al., "A Formalinized Toxoid for Protection of Mice from Inhaled Ricin", Vaccine Research, 4(4): 179-187, 1995.
Kuby et al., "Antigens," *Immunology*, 2:85-96, 1994.
Makarem and Humphries, "LDV: a novel cell adhesion motif recognized by the integrin α4β1," *Biochemical Society Transactions*, 19:380S-381S, 1991.

(Continued)

*Primary Examiner* — Phuong Huynh

(74) *Attorney, Agent, or Firm* — Fulbright & Jaworski L.L.P.

(57) ABSTRACT

The present invention provides methods to produce toxoid vaccines, such as ricin A chain vaccines, with reduced ability to promote vascular leak syndrome (VLS) and catalytic toxicity associated with various proteinaceous toxins, such as ribosome inactivating proteins. The invention also provides toxoids which have been mutated to lack amino acid sequences which induce VLS and toxic catalytic activity.

8 Claims, 10 Drawing Sheets

OTHER PUBLICATIONS

Marsden et al., "The effect of mutations surronding and within the active site on the catalytic activity of ricin A chain," *Eur. J. Biochem.*, 271:153-162, 2004.

Mlsna et al., "Structure of recombinant ricin A chain at 2.3 Å," *Protein Sci.*, 2:429-435, 1993.

Munishkin and Wool, "Systematic deletion analysis of ricin A-chain function," *J. Biol. Chem.*, 270(51):30581-30587, 1995.

Ngo et al., The Protein Folding Problem and Tertiary Prediction, 492-495, 1994.

Nowlin et al., "A novel cyclic pentapeptide inhibits $\alpha 4\beta 1$ and $\alpha 1\beta 1$ integrin-mediated cell adhesion," *J. Biol. Chem.*, 268(27):20352-20359, 1993.

Sausville and Vitetta, "Clinical studies with deglycosylated ricin A-chain immunotoxins," *In: Monoclonal Antibody-Based Therapy of Cancer*, Grossbard (ed.), 4:81-89, 1997.

Skolnick et al., "From genes to protein structure and function: novel applications of computational approaches in the genomic era," *Trends in Biotech*, 18:34-39, 2000.

Soler-Rodriguez et al., "Ricin A-chain and ricin A-chain immunotoxins rapidly damage human endothelial cells: implications for vascular leak syndrome," *Exp. Cell Res.*, 206:227-234, 1993.

Stryer et al., *Biochemistry*, 3:31-33, 1988.

Tagge et al., "Cytotoxicity of KDEL-terminated ricin toxins correlates with distribution of the KDEL receptor in the golgi," *J. of Histochem. and Cytochem.*, 44(2):159-165, 1996.

Yan et al., "Persistence of immunity to ricin toxin evoked by vaccine incorporated into polylactide-CO-glycolide (PLG) microparticles," *Proceed. Intern. Symp. Control. Rel. Bioact. Mater.*, 21(#127):52-53, 1994.

\* cited by examiner

RICIN A CHAIN MUTANTS LACKING ENZYMATIC ACTIVITY AS VACCINES TO PROTECT AGAINST AEROSOLIZED RICIN

The present application is a divisional of application Ser. No. 09/698,551 filed Oct. 26, 2000, now U.S. Pat. No. 7,175,848, which is a continuation-in-part application of U.S. patent application Ser. No. 09/668,419 filed Sep. 22, 2000 now abandoned. The entire texts of the above-referenced disclosures are specifically incorporated by reference herein without disclaimer.

BACKGROUND OF THE INVENTION

1. Field of the Invention

The present invention relates generally to the field of vaccination, and particularly concerns vaccination to protect animals (e.g., humans) against toxins which induce or cause vascular leak syndrome (VLS) and/or catalyze enzymatic activity that damage or kill living cells. The invention provides immunogens which have been mutated to lack amino acid sequences which induce VLS and other toxic side effects. Disclosed are methods for mutating DNA segments encoding antigens so that an immunogen is produced that lacks sequences that induce VLS and other toxic side effects. The present invention also relates the use of mutated toxins as vaccines to protect immunized individuals from later toxicity due to contact with wild-type toxins.

2. Description of Related Art

Vascular leak syndrome (VLS) is a dangerous effect of various toxins and cytokines in animals involving damage to vascular endothelial cells (ECs) and extravasation of fluids and proteins resulting in interstitial edema, weight gain and, in its most severe form, kidney damage, aphasia, and pulmonary edema (Soler-Rodriguez et al., 1993; Sausville and Vitetta, 1997; Baluna and Vitetta, 1996; Engert et al., 1997). The mechanisms underlying VLS are unclear and are likely to involve a cascade of events which are initiated in endothelial cells (ECs) and involve inflammatory cascades and cytokines (Engert et al., 1997). Proteinaceous toxins have been implicated as contributing to vascular leak syndrome (VLS) (Soler-Rodriguez et al., 1993; Baluna et al., 1996). An amino acid motif (x)D(y) has been identified in various proteinaceous toxins and cytokines that contributes to VLS (Baluna et al., 1999). Mutations in this sequence have been shown to reduce the ability of a peptide to produce the effects associated with VLS (Baluna et al., 1999).

In addition to induction of vascular leak syndrome, proteinaceous toxins often catalyze reactions that are detrimental to living cells. One type of enzymatic toxin is ribosome inactivating proteins (RIPs), which comprise various N-glycosylases. Class one RIPs remove a single adenine from a conserved stem loop rRNA sequence (Endo and Tsurugi, 1998). Class two RIPs contain an N-glycosylase and complex to cell surface binding proteins, which enhances cellular uptake. One of the best studied catalytic toxins is ricin, a class two RIP (Mlsna et al., 1993). One active molecule of the A chain of ricin in the cytosol is sufficient to kill a cell (Musishkin and Wool, 1995). Various residues have been identified whose mutation produces catalytically inactive ricin A chain (Mlsna et al., 1993; Musishkin and Wool, 1995).

Several vaccination attempts have been made to protect inviduals from the damage produced by contact with such toxins, including administration of a sub-lethal dose of a toxin (Hewetson et al., 1993), use of a toxoid (Rippy et al., 1991; Hewton et al., 1995) or a sub-unit of a toxin (Lemley et al., 1993). However, despite these attempts, there still remains a need for improved compositions and methods for preparing large amounts of safe and effective proteinaceous toxin vaccines.

SUMMARY OF THE INVENTION

The present invention overcomes the deficiencies in the art by providing methods for reducing the ability of various proteinacious compounds to induce toxic effects. In some embodiments, the invention provides toxoid immunogens with a reduced ability to promote or induce such toxic effects, including, for example, VLS and RIP activity. The present invention also provides methods for reducing the VLS and/or RIP promoting ability of proteinaceous compositions through one or mutations of sequences that induce or promote VLS and/or the catalytic activity of proteinaceous toxins. The present invention provides vaccines to proteinaceous toxins, and methods of preparing such vaccines.

As used herein, a "toxoid" refers to a proteinaceous toxin that has at least one toxic effect reduced or eliminated by heat, chemical treatment and/or mutation of its amino acid sequence, while still retaining most or all of its immunogenicity. Preferred toxoids lack (e.g., comprise a mutation of) at least one (x)D(y) and/or (x)D(y)T sequence, as well as possess mutations that reduce or eliminate a toxic catalytic activity possessed by the wild-type sequence of a proteinaceous toxin.

The invention first provides a method of enhancing an immune response to a proteinaceous toxin, comprising the steps of: obtaining a proteinaceous toxin comprising an amino acid sequence that comprises the sequence (x)D(y), wherein (x) is selected from the group leucine, isoleucine, glycine and valine, and wherein (y) is selected from the group valine, leucine and serine; altering the amino acid sequence that comprises the sequence (x)D(y), altering the active site of the proteinaceous toxin, and contacting the proteinaceous toxin to at least one cell in an amount sufficient to elicit an immune response to the toxin.

The invention also provides a method of enhancing an immune response to a proteinaceous toxin, comprising the steps of: obtaining a nucleic acid encoding a proteinaceous toxin comprising an amino acid sequence that comprises the sequence (x)D(y), wherein (x) is selected from the group leucine, isoleucine, glycine and valine, and wherein (y) is selected from the group valine, leucine and serine; mutating the nucleic acids at a nucleic acid segment encoding the amino acid sequence that comprises the sequence (x)D(y), mutating the nucleic acid at a nucleic acid segment encoding the active site of the proteinaceous toxin, and contacting the nucleic acid with at least one cell, wherein the contacting results in expression of the toxin from the nucleic acid in an amount sufficient to elicit an immune response to the toxin.

The invention further provides a proteinaceous composition that has altered, relative to the sequence of a native proteinaceous composition, at least one amino acid of a sequence comprising (x)D(y), wherein (x) is selected from the group leucine, isoleucine, glycine and valine, and wherein (y) is selected from the group valine, leucine and serine; and has an active site with reduced catalytic activity.

The invention additionally provides a nucleic acid encoding a proteinaceous composition that has altered, relative to the sequence of a native proteinaceous composition, at least one amino acid of a sequence comprising (x)D(y), wherein (x) is selected from the group leucine, isoleucine, glycine and valine, and wherein (y) is selected from the group valine, leucine and serine; and has an active site with reduced catalytic activity.

In some embodiments of the present invention, a toxin is ricin A chain toxin (RTA). In other embodiments of the present invention, a composition or toxin has a reduced ability to induce at least one toxic effect. In other embodiments of the present invention, a toxin is comprised in a vaccine. In some aspects, a toxin is comprised in at least one cell. In certain embodiments, at least one cell is comprised in an animal. In certain aspects, the vaccine comprises at least one additional vaccine component. In particular aspects, the vaccine comprises at least one immunomodulator, adjuvant or carrier.

In certain embodiments of the present invention, an altering comprises at least one mutation of the active site. In some aspects, a mutation alters the ability of at least one residue to function in the active site. In particular facets, a residue is Phe 24, Ile 25, Val 28, Arg 29, Val 81, Val 82, Gly 83, Tyr 84, Glu 146, Ala 147, Ile 148, Ser 149, Phe 168, Ile 169, Ile 170, Cys 171, Ile 172, Gln 173, Ile 175, Ser 176, Glu 177, Ala 178, Ala 179, Arg 180, Phe 181, Gln 182, Tyr 183, Ile 184, Pro 202, Ser 203, Thr 206, Leu 207, Ser 210, Trp 211, Gly 212 or Arg 213 of SEQ ID NO:1. In some embodiments of the present invention, the active site is removed.

In particular embodiments, the altering comprises at least one mutation of the amino acid sequence. In certain aspects, the altering comprises at least one mutation of the amino acid sequence. In some embodiments, an (x)D(y) sequence comprises the LDV sequence at positions 74 to 76 of SEQ ID NO:1. In other embodiments, the amino acid sequence is removed. In other aspects, the (x)D(y) sequence is GDL, GDS, GDV, IDL, IDS, IDV, LDL, LDS, LDV, LDS, VDL or VDV. In some aspects, the (x)D(y) sequence comprises at least one residue on the surface of the composition. In additional facets, the altering occurs at one or more (x)D(y) tri-amino acid sequences.

In further facets, the (x)D(y) sequence comprises at least one flanking sequence. In other facets, the flanking sequence is C-terminal to the (x)D(y) sequence. In particular facets, the flanking sequence is N-terminal to the (x)D(y) sequence. In additional facets, at least one flanking sequence comprises two flanking sequences, wherein the two flanking sequences are N-terminal and C-terminal to the (x)D(y) sequence. In specific facets, altering the sequence comprises at least one alteration within the at least one flanking sequence. In particular facets, at least one flanking sequence is mutated. In some facets, at least one flanking sequence is removed.

Product toxoid.

Product toxoid obtainable by a process described herein.

Product toxoid for use as a medicament.

Use of compound proteinaceous toxoid for the manufacture or a medicament for the treatment of a toxic effect.

A method for manufacturing a product toxoid comprising the steps of obtaining a proteinaceous toxin comprising an amino acid sequence that comprises the sequence (x)D(y), wherein (x) is selected from the group leucine, isoleucine, glycine and valine, and wherein (y) is selected from the group valine, leucine and serine; altering the amino acid sequence that comprises the sequence (x)D(y), altering the active site of the proteinaceous toxin.

As used herein, "any range derivable therein" means a range selected from the numbers described in the specification, and "any integer derivable therein" means any integer between such a range.

As used herein the specification, "a" or "an" may mean one or more. As used herein in the claim(s), when used in conjunction with the word "comprising", the words "a" or "an" may mean one or more than one. As used herein "another" may mean at least a second or more.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1A) SCID mice with human skin xenografts were injected with 200 μg of RFB4-dgRTA (open), RFB4-LDV+ (cross-hatched), RFB4-GQT (hatched) or saline (solid), and the wet/dry weight ratios of the human skin were determined. (FIG. 1B) SCID mice were injected as described in FIG. 1A and the wet/dry weight ratios of lungs were determined. The values represent the mean of three experiments±SD. The asterisks indicate a statistically significant difference from saline-treated mice (*, $p<0.02$, ** $p<0.01$).

(FIG. 2A) $10^5$ HUVECs were incubated on ice for 30 min with FITC-dgRTA, in the presence or absence of 100-fold excess of dgRTA (solid), RFB4-LDV+ (crosshatched), RFB4 (shaded), Fn (hatched) or PE38-lys (open) in 100 ul PBS/BSA/Azide. The percent inhibition of binding to HUVECs is presented. The values represent the means±SD of three studies. (FIG. 2B) The same as FIG. 2A, except the $10^5$ HUVECs were incubated on ice for 30 min with FITC-RFB4-LDV+.

(FIG. 5A) The body weights were determined. (FIG. 5B) The wt/dry wt ratio of lungs were determined.

DESCRIPTION OF ILLUSTRATIVE EMBODIMENTS

Figure 1B:
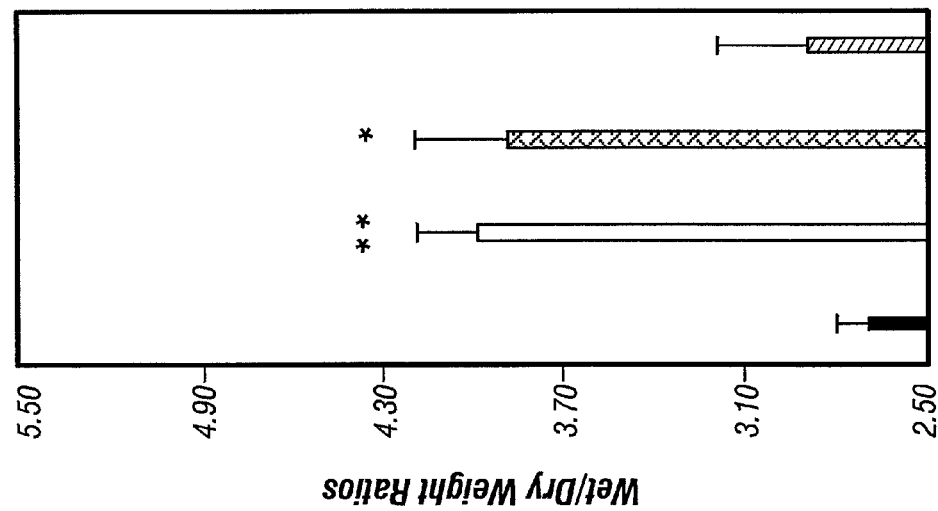
FIGS. 1A and 1B. The in vivo effect of RFB4-RTA-peptides.
Figure 1A:
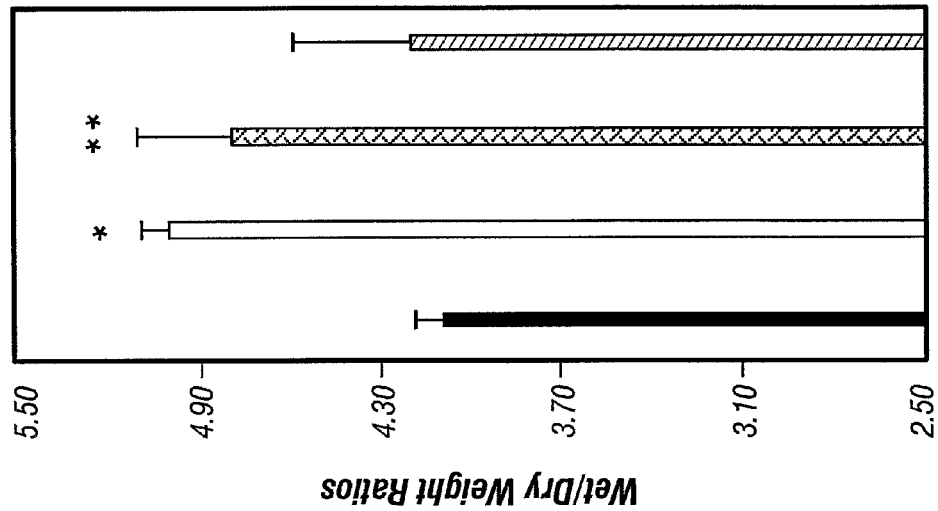
Figure 2A:
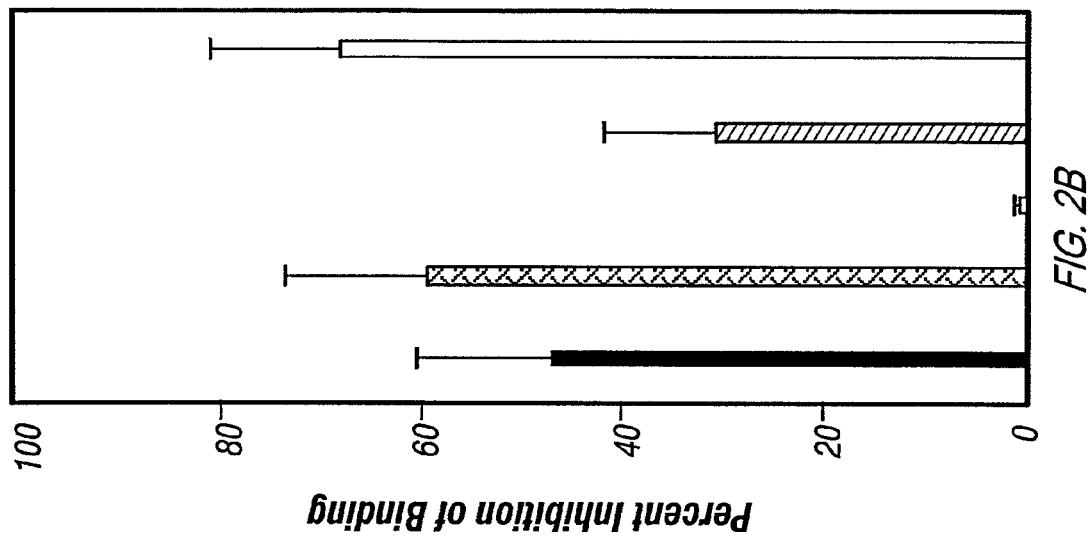
FIGS. 2A and 2B. Inhibition of the binding of dgRTA and RFB4-LDV+ to HUVECs.
Figure 2B:
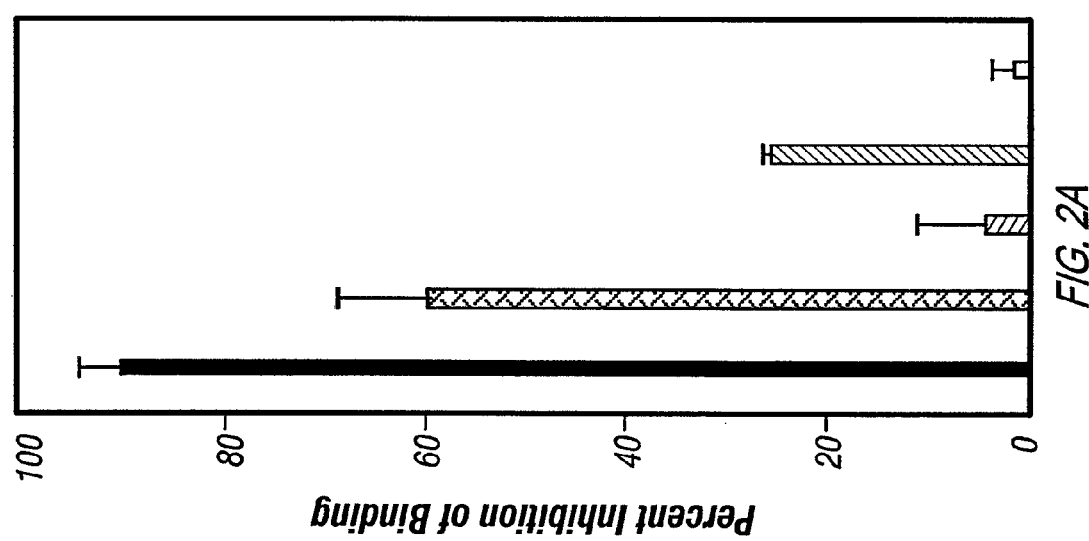

Cell damage, particularly endothelial cell (EC) damage, produced by toxins such as ricin A chain, is a danger for individuals who have contact with such toxins. Individuals that are in danger of such contact include members of the armed services, as well as civilians, who may be exposed to chemical weapons or terrorist devices.

To develop effective and safe vaccines to such proteinaceous toxins, a (x)D(y) consensus motif responsible for inducing VLS was identified, where (x) could be L, I, G or V and (y) could be V, L or S, in various proteinaceous toxins. In the case of RTA, molecular modeling indicated that these motifs were completely or substantially exposed on the surface of the molecule. A similar motif is shared by viral disintegrins, which disrupts the function of integrins, and IL-2, which causes vascular leak syndrome, indicating that RTA, IL-2 and perhaps other toxins may damage ECs by virtue of their (x)D(y) motifs and hence, may be disintegrins.

The vascular-leak-promoting activity of this motif was surprising and unexpected, since LDV homologue sequences also play a role in the vascular functions of a variety of non-toxic molecules including vascular cell adhesion molecule 1 (VCAM-1), which contains the IDS sequence, and the γ chain of fibrinogen, which contains the GDV sequence (Clements et al., 1994). LDV constitutes the minimal active site in the CS1 domain of fibronectin responsible for its binding to the $\alpha_4\beta_1$ integrin receptor (Makarem and Humphries, 1991; Wayner and Kovach, 1992; Nowlin et al., 1993). Though fibronectin possesses this sequence, it does not damage HUVECs. Instead, FN protects HUVECs from RTA-mediated damage (Baluna et al., 1996), in direct contrast to the VLS activity of toxic agents that possess this motif.

To determine whether this motif was responsible for EC damage, short LDV- or LDL-containing peptides from RTA or IL-2, respectively, were generated, attached to a mouse MAb and studied for their ability to bind to and damage HUVECs in vitro and to damage mouse lung vasculature and human vasculature in human skin xenografts in vivo. One active site mutant of RTA and several LDV mutant peptides were generated. These LDV mutants contained conservative changes which, when modeled, would not be expected to affect the active site of the RTA. Antibody-conjugated peptides from RTA containing the sequence (L74, D75, V76), but not peptides with deleted or altered sequence, induced EC damage in vitro and vascular damage in vivo in the two animal models (Baluna et al., 1999). These results demonstrated that the VLS-inducing site does not require the active site. It is contemplated that the noncontiguous active site of the RTA, which does not encompass LDV, is either not required to damage ECs, or only partly contributes to vascular damage.

These results demonstrate that one or more peptides or polypeptides may be made with reduced VLS promoting activity. With this discovery, it is now possible that one or more amino acid deletion(s) or mutation(s) of the (x)D(y) sequence(s), and/or at least one region flanking the sequence, may reduce or prevent VLS and improve the therapeutic index or the tolerated dose of VLS-inducing molecules. It is expected that one or more peptides and small molecule drug inhibitors comprising at least one mutated motif and/or one or more flanking sequence can be created that reduce or eliminate the VLS induced by VLS promoting agents.

Additionally, various residues important in maintaining the destructive enzymatic activity of toxins, such as ricin A chain, have been identified (Mlsna et al., 1993; Musishkin and Wool, 1995). Mutations in these residues, described herein, may be made to produce enzymatically inactive or attenuated toxoids.

By producing double mutations in proteinaceous toxins to reduce or eliminate both the ability of the toxin to induce VLS (i.e., apoptotic activity, EC damaging and/or one or more disintegrin-like activities) and catalyze toxic reactions (i.e., ribosome inactivation) in cells, the invention provides new and superior toxoids that may be used to safely vaccinate individuals against deadly toxins. Such toxoid immunogens and vaccines are described herein, as are methods of producing such immunogenic compositions and vaccines.

A. Identification of an (X)D(Y) Motif in VLS-Inducing Agents

Homologous structural motifs in RTA, other toxins, RIPs and IL-2 (SEQ ID NO:2), which may affect cell-cell and cell-matrix interactions and thereby damage human ECs, have been identified and tested for their ability to promote VLS in model systems. The (x)D(y) motif where x=L, I, G or V and y=V, L or S is common in the sequences of RTA, other toxins, RIPs and cytokines which induce VLS. This motif is also shared by viral disintegrins which disrupt the function of integrins (Coulson et al., 1997). Table 1 shows the position of this sequence in various toxins.

TABLE 1

Non-Limiting Examples of (x)D(y) Motifs in Molecules Which Induce VLS

| Category | Agent inducing VLS | (X) D(Y) Motif | Location | GenBank or GenPept Accession # |
|---|---|---|---|---|
| Toxins[1] | Ricin Toxin A-Chain (RTA) | LDV | 74-76 | A23903 |
| | Abrin A chain | IDV | 68-70 | X76721 |
| | | GDL | 114-116 | |
| | | VDS | 229-231 | |
| | Barley toxin | LDV | 171-173 | U77463 |
| | Diphtheria Toxin (DT) A-Chain | VDS | 6-8 | 576189 |
| | | VDS | 28-30 | |
| | | IDS | 289-291 | |
| | | LDV | 441-443 | |
| | Pseudomonas exotoxin-(PE38-lys)[2] | GDL | 348-350 | K01397 |
| | | GDV | 430-432 | |
| | | GDL | 605-607 | |
| | Shiga toxin A chain | VDS | 36-38 | M19437 |
| | | IDS | 63-65 | |
| | | VDV | 74-76 | |
| | | GDS | 132-134 | |
| | | LDL | 162-164 | |
| | | VDL | 219-221 | |
| RIPs[3] | Gelonin | IDV | 114-116 | L12243 |
| | Momordin | LDV | 64-66 | 576194 |
| | | LDS | 132-134 | |
| | Momordin | LDS | 165-167 | P16094 |
| | Pokeweed Antiviral Protein (PAP) | VDS | 179-181 | X98079 |
| | | GDL | 308-310 | |
| | Saporin | LDL | 6-8 | X69132 |
| | | IDL | 143-145 | |
| | Trichosanthin | GDV | 23-25 | U25675 |
| | | IDV | 87-89 | |
| | | LDS | 155-157 | |

[1]The enzymatically active chain of the holotoxin
[2]PE38 refers to enzymatically active Domain III (residues 405 to 613) plus residues 253-354 and 381-404 in PE.
[3]Ribosome-inactivating proteins (RIPs) which are homologues of the enzymatically active A chain of plant toxins 1. Localization of (x)D(y) Motifs in RTA With the discovery of the importance of the (x)D(y) sequence in promoting VLS, it is now possible to create toxin mutants which have their VLS-inducing properties reduced.

For example, the LDV motif in RTA (residues 74-76, SEQ ID NO:1) is at the C-terminus of a β-strand of the first domain near the Tyr-80 residue which is involved in the active site (Mlsna et al., 1993). The active site (residues Y80, Y123, E177, R180, N209, W211) of the enzyme does not include the LDV sequence so that the enzymatic activity of RTA should not be affected by mutations or deletions in this sequence (Munishkin and Wool, 1995).

To examine the crystal structure of RTA, space filling models of the three dimensional structures of RTA were made (PDB accession number 1br5.pdb). The model was generated with the Insight II program (MSI). Examinations of the crystal structure of RTA indicate that this motif is only partially exposed, but structural fluctuations in the molecule may increase its accessibility. From this and other data described herein, it is contemplated that either alterations in the (x)D(y) motif, the C-terminal flanking amino acid(s), the N-terminal flanking amino acid(s), or a combination thereof, may result in the loss or attenuation of VLS-inducing activity.

2. Mutations in Flanking Sequences

The (x)D(y) sequence may not be solely responsible for the promotion of VLS. In certain embodiments, it is contemplated that additional sequences that flank the (x)D(y) sequence or are distastal from the sequences but affect its exposure on the molecule may be mutated to enhance or reduce a peptide, polypeptide or protein's ability to promote VLS.

For example, LDV constitutes the minimal active site in the CS1 domain of fibronectin responsible for its binding to the $\alpha_4\beta_1$ integrin receptor (Makarem and Humphries, 1991; Wayner and Kovach, 1992; Nowlin et al., 1993). However, fibronectin (FN) does not damage HUVECs. Instead, FN protects HUVECs from RTA-mediated damage (Baluna et al., 1996). Unlike RTA, FN has a C-terminal LDV-flanking proline instead of a threonine. Therefore, a change in one or more amino acids of this sequence or one or more amino acids of the N- or C-terminal flanking sequences may convert a molecule from one that damages endothelial cells (distintegrin-like) to one that enhances their growth. It is contemplated that changes in one or more flanking residues or distal residues of the (x)D(y) sequence may enhance or reduce the ability of a molecule to promote VLS. It is further contemplated that changes that expose the (x)D(y) sequence to the external surface of the protein so as to interact with other proteins, such as receptors, would enhance VLS promoting activity, while conformations that are less exposed may reduce VLS promoting activity.

B. Toxoids with Reduced VLS Activity

With the identification of the (x)D(y) and the (x)D(y)T motifs as inducing VLS, inducing apoptosis, and other effects, it is possible that the creation of a new family of immunogenic molecules will allow these molecules to exert maximal beneficial effects. For example, the LDV in RTA may be altered to reduce or eliminate VLS activity.

To produce peptides, polypeptides or proteins that lack the (x)D(y) and/or (x)D(y)T sequence, one could delete the conserved aspartic acid (D), substitute another amino acid for the aspartic acid, or insert one or more amino acids at or adjacent to its position. Any other amino acid may replace the (D) residue in the sequence as a consequence of a deletion or mutation event to reduce the sequence's activity.

Alternatively the (x) residue could be deleted, substituted, or moved by the insertion of one or more amino acids, to alter the (x)D(y) and/or (x)D(y)T sequence. Any amino acid that may replace the (x) residue in the sequence as a consequence of the deletion or mutation event is preferably not leucine (L), isoleucine (I), glycine (G) or valine (V).

Or the (y) residue could be deleted, substituted, or moved by the insertion of one or more amino acids, to alter the (x)D(y) and/or (x)D(y)T sequence. Any amino acid that may replace the (y) residue in the sequence as a consequence of the deletion or mutation event is preferably not valine (V), leucine (L) or serine (S).

Additionally, the (x)D(y) and/or (x)D(y)T sequences can be removed by any mutation that alters or changes this sequence. Such mutations include but are not limited to truncations, insertions, substitutions and deletions of amino acids. It is contemplated that chemical modification may also alter a (x)D(y) and/or (x)D(y)T sequence to reduce its ability to induce or promote VLS.

Thus, it is contemplated that such mutations that affect the (x)D(y) sequence or flanking sequence may alter the ability of a polypeptide to promote VLS or other abilities associated with these sequences. For example, one preferred agent that produced VLS is ricin A chain (SEQ ID NO:1), which contains an LDV sequence at positions 74-76 of its amino acid sequence. It is a mutation, such as, for example, in the aspartate at position 75 to convert it to a glutamate would produce an immunologically functional equivalent sequence while reducing or eliminating its VLS promoting activity. Of course, various other types of mutations may be done to either reduce VLS activity and/or produce an immunologically functional equivalent, using the techniques described herein or as would be known to one of ordinary skill in the art.

In another example, one agent that produces VLS is abrin A chain (GenBank Accession number X76721; SEQ ID NO:3), which contains an IDV sequence at positions 68-70 of its amino acid sequence. A glycine (G) is at position 67. Therefore, a deletion of the isoleucine at position 68 would result in the glycine at position 67 to be directly adjacent to the aspartic acid residue (D) at original position 69. The new sequence created would then be GDV at positions 67-69 of the mutated abrin A chain. This new tripeptide sequence still matches the putative VLS-inducing sequence (x)D(y) and/or (x)D(y)T. However, it is contemplated that since such a deletion would shift the position of the tri-amino acid sequence in the structure of the mutated abrin A chain protein, polypeptide or peptide being produced. A shift in the position of the tri-amino acid sequence may move it into a less favorable position to contact any cell, receptor or molecule to promote or induce VLS. The resulting mutated abrin A chain protein, polypeptide or peptide may have a reduced ability to promote or induce VLS, and thus would be encompassed by the present invention.

Similarly, other toxins or compounds that induce VLS, including but not limited to those listed in Table 1, can be mutated so that one or more (x)D(y) and/or one or more flanking residues are removed (i.e., mutated). However, it is contemplated that to produce toxins or compounds that have a reduced ability to induce VLS, that any remaining (x)D(y) and/or (x)D(y)T sequences should have a reduced exposure to the surface of the protein, polypeptide or peptide.

For example, it is contemplated that (x)D(y) and/or (x)D(y)T sequences that are at least partly located in the non-exposed portions of a protein, polypeptide or peptide, or otherwise masked from full or partial exposure to the surface of the molecule, would interact less with cells, receptors or other molecules to promote or induce VLS. Thus, it is contemplated that the complete elimination of (x)D(y) and/or (x)D(y)T sequences from the primary structure of the protein, polypeptide or peptide is not necessary to produce toxins or molecules with a reduced ability to induce or promote VLS. However, removal of all (x)D(y) and/or (x)D(y)T sequences is preferred to insure the composition has the least ability to induce or promote VLS.

To determine whether a mutation would likely produce a protein, polypeptide or peptide with a less exposed (x)D(y) and/or (x)D(y)T motif, the putative location of the moved or added (x)D(y) and/or (x)D(y)T sequence could be determined by comparison of the mutated sequence to that of the unmutated protein, polypeptide or peptide's secondary and tertiary structure, as determined by such methods known to those of ordinary skill in the art including, but not limited to, X-ray crystallography, NMR or computer modeling. Computer models of various polypeptide and peptide structures are also available in the literature or computer databases. In a non-limiting example, the Entrez database (http://www.ncbi.nlm.nih.gov/Entrez/) may be used by one of ordinary skill in the art to identify target sequences and regions for mutagenesis. The Entrez database is crosslinked to a database of 3-D structures for the identified amino acid sequence, if known. Such molecular models may be used to identify (x)D (y), (x)D(y)T and/or flanking sequences in peptides and polypeptides that are more exposed to contact with external molecules, (e.g. receptors) than similar sequences embedded in the interior of the polypeptide or polypeptide. It is contemplated that (x)D(y), (x)D(y)T and/or flanking sequences that are more exposed to contact with external molecules are more likely to contribute to promoting or reducing VLS and other toxic effects associated with these sequences, and thus should be primary targets for mutagenesis. The mutated or wild-type protein, polypeptide or peptide's structure could be determined by X-ray crystallography or NMR directly before use in in vitro or in vivo assays, as would be known to one of ordinary skill in the art.

Once an amino acid sequence comprising a (x)D(y) and/or (x)D(y)T sequence is altered in a peptide, polypeptide or protein, or removed from to a peptide, polypeptide or protein, changes in its ability to promote at least one toxic effect may be assayed by any of the techniques described herein or as would be known to one of ordinary skill in the art.

As used herein, "alter", "altered", "altering", "alteration" of an amino acid sequence comprising a (x)D(y) sequence or a (x)D(y)T sequence may include chemical modification of an amino acid sequence comprising a (x)D(y) and/or a (x)D (y)T sequence in a protein, polypeptide or peptide as would be known to those of ordinary skill in the art, as well as any mutation of such an amino acid sequence including but not limited to insertions, deletions, truncations, or substitutions. It is preferred that such changes alters at least one toxic effect (i.e., the ability to promote VLS, EC damage, apoptosis, disintigrin-like activity) of one or more amino acid sequence(s) comprising a (x)D(y) and/or (x)D(y)T sequences. As used herein an amino acid sequence comprising a (x)D(y) sequence or a (x)D(y)T sequence may comprise at least one flanking sequence C- and/or N-terminal to a (x)D(y) and/or a (x)D(y)T tri- or tetra-peptide sequence. Such an "alteration" may be made in synthesized peptides, or in nucleic acid sequences that are expressed to produce mutated proteins, polypeptides or peptides.

In an aspect of the invention, the alteration of an amino acid sequence comprising a (x)D(y) and/or a (x)D(y)T sequence comprises removal of the amino acid sequence. As used herein "remove", "removed", "removing" or "removal" of an amino acid sequence comprising a (x)D(y) and/or a (x)D(y)T sequence refers to a mutation in the primary amino acid sequence that eliminates the presence of the (x)D(y) and/or a (x)D(y)T tri- or tetra-peptide sequence, and/or at least one native flanking sequence. The terms "removed" or "lacks" may be used interchangably.

For example, it is contemplated that mutations including but not limited to at least one insertion or substitution of at least one amino acid selected from the group phenylalanine (F); cysteine (C); methionine (M); alanine (A); threonine (T); serine (S); tryptophan (W); tyrosine (Y); proline (P); histidine (H); glutamic acid (E); glutamine (Q); aspartic acid (D); asparagine (N); lysine (K); and arginine (R), and including, but not limited to, those shown at Table 2 at the position (x) of one or more (x)D(y) and/or (x)D(y)T sequences would reduce its ability to promote VLS. Table 2 below lists exemplary, but not limiting, modified or unusual amino acids that are contemplated as useful in certain aspects of the invention.

TABLE 2

Modified and Unusual Amino Acids

| Abbr. | Amino Acid | Abbr. | Amino Acid |
|---|---|---|---|
| Aad | 2-Aminoadipic acid | EtAsn | N-Ethylasparagine |
| Baad | 3-Aminoadipic acid | Hyl | Hydroxylysine |
| Bala | β-alanine, β-Amino-propionic acid | Ahyl | Allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Hydroxyproline |
| Acp | 6-Aminocaproic acid | Ide | Isodesmosine |
| Ahe | 2-Aminoheptanoic acid | Aile | Allo-Isoleucine |
| Aib | 2-Aminoisobutyric acid | MeGly | N-Methylglycine, sarcosine |
| Baib | 3-Aminoisobutyric acid | MeIle | N-Methylisoleucine |
| Apm | 2-Aminopimelic acid | MeLys | 6-N-Methyllysine |
| Dbu | 2,4-Diaminobutyric acid | MeVal | N-Methylvaline |
| Des | Desmosine | Nva | Norvaline |
| Dpm | 2,2'-Diaminopimelic acid | Nle | Norleucine |
| Dpr | 2,3-Diaminopropionic acid | Orn | Ornithine |
| EtGly | N-Ethylglycine | | |

It is also contemplated that mutations including but not limited to at least one insertion or substitution of at least one amino acid selected from the group isoleucine (I); valine (V); leucine (L); phenylalanine (F); cysteine (C); methionine (M); alanine (A); glycine (G); threonine (T); serine (S); tryptophan (W); tyrosine (Y); proline (P); histidine (H); glutamic acid (E); glutamine (Q); asparagine (N); lysine (K); and arginine (R), and including, but not limited to, those shown at Table 2 at the position (D) of one or more (x)D(y) and/or (x)D(y)T sequences would reduce its ability to promote VLS.

It is contemplated that mutations including but not limited to at least one insertion or substitution of at least one amino acid selected from the group isoleucine (I); phenylalanine (F); cysteine (C); methionine (M); alanine (A); glycine (G); threonine (T); tryptophan (W); tyrosine (Y); proline (P); histidine (H); glutamic acid (E); glutamine (Q); aspartic acid (D); asparagine (N); lysine (K); and arginine (R), and including, but not limited to, those shown at Table 2 at the position (y) of one or more (x)D(y) and/or (x)D(y)T sequences would reduce its ability to promote VLS.

Amino acids that flank either the (x) or (y) residue of the (x)D(y) sequence may also contribute to its ability to promote VLS. For example, is it contemplated that mutations including but not limited to at least one insertion or substitution of at least one amino acid selected from the group isoleucine (I); valine (V); leucine (L); phenylalanine (F); cysteine (C); methionine (M); alanine (A); glycine (G); serine (S); tryptophan (W); tyrosine (Y); proline (P); histidine (H); glutamic acid (E); glutamine (Q); aspartic acid (D); asparagine (N); lysine (K); and arginine (R), and including, but not limited to, those shown at Table 2 at the position T of one or more (x)D(y)T sequences would reduce its ability to promote VLS.

It is further contemplated that at least one mutation, chemical modification, movement or other alteration in the N- or C-terminal flanking sequences of the (x)D(y) and/or (x)D (y)T sequence would also produce proteins, polypeptides or peptides that have a reduced ability to promote VLS. In other embodiments, the mutations or alterations would occur in one or more residues of from about 1, about 2, about 3, about 4, about 5, about 6 or more N-terminal and/or C-terminal to the (x)D(y) tripeptide sequence. In other aspects, one or more residues that are not adjacent to the (x)D(y) tripeptide may contribute to the function of the (x)D(y) motif. Such residues may be identified by their proximity to the tripeptide sequence in a 3-dimensional model, as described herein and as would be known to one of ordinary skill in the art, and are contemplated for alteration as part of a flanking sequence. Such alterations may include any of those described above for altering the (x)D(y) and (x)D(y)T sequences, as long as one or more "wild type" flanking residues are altered, removed, moved, chemically modified, or otherwise mutated.

Proteins, polypeptides and peptides produced using the methods of the present invention that have a reduced ability to induce VLS would have application in serving as vaccine agents against VLS produced by compositions containing the (x)D(y) and/or (x)D(y)T sequence. It is contemplated that such proteins, polypeptides and peptides may serve as inhibitors that block the activity of the (x)D(y) and/or (x)D(y)T sequence. Additionally, such proteins, polypeptides and peptides may be used in the creation of vaccines with a reduced ability to produce VLS.

C. Toxoids with Reduced Enzymatic Activity

In addition to alterations in the (x)D(y) and flanking sequences associated with VLS, the present invention provides immunogenic compositions of toxoids wherein the toxin is mutated to reduce or eliminate the enzymatic activity that contributes to its detrimental cellular effects. The active site of various toxins, such as, for example, RIPs, have been identified, and it is contemplated that any mutation that disrupts the active site by altering protein compositions or conformations may be used to produce such a toxoid. In certain preferred embodiments, one or more residues important in maintaining the catalytic site's structure or participate in chemical reactions catalyzed by the toxin are specifically targeted for mutation. Preferred mutations are those that maintain or enhance the immunogenicity of the toxoid relative to the wild-type toxin, i.e., produce an immunologically functional equivalent. It is contemplated that any technique descibed herein, such as, for example, those used to mutate the (x)D(y) sequence, or that would be known to one of skill in the art, may be used to produce such a toxoid.

In a non-limiting example, one may mutate the residues known to be important directly or indirectly, catalytically or structurally in the active site of ricin A chain to produce a toxid with reduced or absent catalytic activity. In certain aspects, such residues include one or more of the following: Asn 209, Glu 177, Trp 211, Tyr 80, Tyr 123 or Arg 180 (Mlsna et al., 1993). However, in more preferred aspects, such residues include at least one of the following: Phe 24, Ile 25, Val 28, Arg 29, Val 81, Val 82, Gly 83, Tyr 84, Glu 146, Ala 147, Ile 148, Ser 149, Phe 168, Ile 169, Ile 170, Cys 171, Ile 172, Gln 173, Ile 175, Ser 176, Glu 177, Ala 178, Ala 179, Arg 180, Phe 181, Gln 182, Tyr 183, Ile 184, Pro 202, Ser 203, Thr 206, Leu 207, Ser 210, Trp 211, Gly 212 or Arg 213 (Munishkin and Wool, 1995).

D. Vaccines

The present invention contemplates vaccines for use in immunization embodiments. It is contemplated that compositions that are less effective in promoting VLS or other toxic effects by alterations in one or more (x)D(y), (x)D(y)T and/or flanking sequences may be useful as immunogens for vaccine preparations. In preferred embodiments, proteinaceous toxiod compositions lacking one or more (x)D(y), (x)D(y)T and/or flanking sequences and at comprising at least one mutation in the active site, nucleic acids encoding and/or cells expressing such proteinaceous compositions are contemplated as useful immunogens. It is particularly preferred that such mutations produce immunologically functional equivalent sequences.

In certain aspects, mutagenesis of peptides, polypeptides or proteins, or nucleic acids encoding peptides, polypeptides or proteins may be used to produce the desired mutations to reduce a composition's ability to promote VLS, apoptosis or other effects associated with the (x)D(y) and flanking sequences, as well as inactivate the ability of the known active site of a toxin to produce detrimental biological effects. Mutagenesis may be conducted by any means disclosed herein or known to one of ordinary skill in the art.

For an immunogenic composition to be useful as a vaccine, an immunogenic composition or the present invention must induce an immune response to the immunogen in at least one cell, tissue or animal (e.g., a human). As used herein, an "immunogenic composition" may comprise an immunogen (e.g., a peptide or polypeptide), a nucleic acid encoding an immunogen (e.g., an immunogen expression vector), or at least one cell expressing or presenting an immunogen. In particular embodiments the immunogenic composition comprises or encodes all or part of the sequence shown in SEQ ID NO:1, or an immunologically functional equivalent thereof. In other embodiments, the immunogenic composition is in a mixture that comprises an additional immunostimulatory agent or nucleic acids encoding such an agent separately or as a fusion. Immunostimulatory agents include but are not limited to an additional immunogen, an immunomodulator, an antigen presenting cell or an adjuvant. In other embodiments, one or more of the additional agent(s) is covalently bonded to the antigen or an immunostimulatory agent, in any combination. In certain embodiments, the immunogenic composition is conjugated to or comprises an HLA anchor motif amino acids.

In certain embodiments, an immunogenic composition or immunologically functional equivalent, may be used as an effective vaccine in inducing an anti-toxin humoral and/or cell-mediated immune response in an animal. The present invention contemplates one or more immunogenic compositions or vaccines for use in both active and passive immunization embodiments. For example, in one passive immunization embodiment one may administer a monoclonal antibody directed against a composition of the present invention. However, in general embodiments an immunogenic composition will be administered to elicit an active immune response against the immunogenic composition.

A vaccine of the present invention may vary in its composition of proteinaceous, nucleic acid and/or cellular components. In a non-limiting example, a nucleic acid encoding an immunogen might also be formulated with a proteinaceous adjuvant. Of course, it will be understood that various compositions described herein may further comprise additional components. For example, one or more vaccine components may be comprised in a lipid or liposome. In another non-limiting example, a vaccine may comprise one or more adjuvants. A vaccine of the present invention, and its various components, may be prepared and/or administered by any method disclosed herein or as would be known to one of ordinary skill in the art, in light of the present disclosure.

1. Proteinaceous Antigens

It is understood that an immunogenic composition of the present invention may be made by a method that is well known in the art, including but not limited to chemical synthesis by solid phase synthesis and purification away from the other products of the chemical reactions by HPLC, or production by the expression of a nucleic acid sequence (e.g., a DNA sequence) encoding a peptide or polypeptide comprising an immunogen of the present invention in an in vitro translation system or in a living cell. Preferably the immunogenic composition is isolated and extensively dialyzed to remove one or more undesired small molecular weight molecules and/or lyophilized for more ready formulation into a desired vehicle. It is further understood that additional amino acids, mutations, chemical modification and such like, if any, that are made in a vaccine component will preferably not interfere with the antibody recognition of epitopic sequence(s).

A peptide or polypeptide corresponding to one or more immunogenic determinants of the toxin immunogen of the present invention should generally be at least five or six amino acid residues in length, and may contain up to about 10, about 15, about 20, about 25 about 30, about 35, about 40, about 45 or about 50 residues. In certain embodiments, one or more specific residues that comprise an immunogenic determinant may not be contiguous with another residue that comprises an immunogenic determinant. A peptide sequence may be synthesized by methods known to those of ordinary skill in the art, such as, for example, peptide synthesis using automated peptide synthesis machines, such as those available from Applied Biosystems (Foster City, Calif.).

Longer peptides or polypeptides also may be prepared, e.g., by recombinant means. In certain embodiments, a nucleic acid encoding an immunogenic composition and/or a component described herein may be used, for example, to produce an immunogenic composition in vitro or in vivo for the various compositions and methods of the present invention. For example, in certain embodiments, a nucleic acid encoding an immunogen is comprised in, for example, a vector in a recombinant cell. The nucleic acid may be expressed to produce a peptide or polypeptide comprising an immunogenic sequence. The peptide or polypeptide may be secreted from the cell, or comprised as part of or within the cell. In certain embodiments, the peptide or polypeptide is purified from the cell or cellular components.

2. Genetic Vaccine Antigens

In certain embodiments, an immune response may be promoted by transfecting or inoculating an animal with a nucleic acid encoding an immunogen. One or more cells comprised within a target animal then expresses the sequences encoded by the nucleic acid after administration of the nucleic acid to the animal. Thus, the vaccine may comprise "genetic vaccine" useful for immunization protocols. Expression in vivo by the nucleic acid may be, for example, by a plasmid type vector, a viral vector, or a viral/plasmid construct vector.

In preferred aspects, the nucleic acid comprises a coding region that encodes all or part of the sequences disclosed as SEQ ID NO:1, or an immunologically functional equivalent thereof. Of course, the nucleic acid may comprise and/or encode additional sequences, including but not limited to those comprising one or more immunomodulators or adjuvants. The nucleotide and protein, polypeptide and peptide sequences for various genes have been previously disclosed, and may be found at computerized databases known to those of ordinary skill in the art. One such database is the National Center for Biotechnology Information's Genb ank and GenPept databases (http://www.ncbi.nlm.nih.gov/). The coding regions for these known genes may be amplified, combined with the toxin sequences disclosed herein (e.g., ligated) and/or expressed using the techniques disclosed herein or by any technique that would be know to those of ordinary skill in the art (e.g., Sambrook et al., 1987). Though a nucleic acid may be expressed in an in vitro expression system, in preferred embodiments the nucleic acid comprises a vector for in vivo replication and/or expression.

3. Cellular Vaccine Antigens

In another embodiment, at least one cell expressing the immunogen may comprise the vaccine. The cell may be isolated from a culture, tissue, organ or organism and administered to an animal as a cellular vaccine. Thus, the present invention contemplates a "cellular vaccine." The cell may be transfected with a nucleic acid encoding an immunogen to facilitate its expression of the immunogen. Of course, the cell may also express one or more additional vaccine components, such as immunomodulators or adjuvants. A vaccine may comprise all or part of the cell.

In particular embodiments, it is contemplated that nucleic acids encoding antigens of the present invention may be transfected into plants, particularly edible plants, and all or part of the plant material used to prepare a vaccine, such as, for example, an oral vaccine. Such methods are described in U.S. Pat. Nos. 5,484,719, 5,612,487, 5,914,123, 5,977,438 and 6,034,298, each incorporated herein by reference.

4. Immunologically Functional Equivalents

As modifications and changes may be made in the structure of an immunogenic composition (e.g., a toxin immunogen) of the present invention, and still obtain molecules having like or otherwise desirable characteristics, such immunologically functional equivalents are also encompassed within the present invention.

For example, certain amino acids may be substituted for other amino acids in a peptide, polypeptide or protein structure without appreciable loss of interactive binding capacity with structures such as, for example, antigen-binding regions of antibodies, binding sites on substrate molecules or receptors, DNA binding sites, or such like. Since it is the interactive capacity and nature of a peptide, polypeptide or protein that defines its biological (e.g., immunological) functional activity, certain amino acid sequence substitutions can be made in a amino acid sequence (or, of course, its underlying DNA coding sequence) and nevertheless obtain a peptide or polypeptide with like (agonistic) properties. It is thus contemplated by the inventors that various changes may be made in the sequence of an immunogenic composition such as, for example a toxin immunogen peptide or polypeptide, or underlying DNA, without appreciable loss of biological utility as an immunogen to stimulate an immune response to the wild-type toxin.

As used herein, an "amino acid molecule" refers to any amino acid, amino acid derivative or amino acid mimic as would be known to one of ordinary skill in the art. In certain embodiments, the residues of the immunogenic composition comprises amino acid molecules that are sequential, without any non-amino acid molecule interrupting the sequence of amino acid residues. In other embodiments, the sequence may comprise one or more non-amino acid moieties. In particular embodiments, the sequence of residues of the immunogenic composition may be interrupted by one or more non-amino acid moieties.

Accordingly, immunogenic composition, particularly an immunologically functional equivalent of the sequences disclosed herein, may encompass an amino acid molecule sequence comprising at least one of the 20 common amino acids in naturally synthesized proteins, or at least one modified or unusual amino acid, including but not limited to those shown on Table 2.

In terms of immunologically functional equivalent, it is well understood by the skilled artisan that, inherent in the definition is the concept that there is a limit to the number of changes that may be made within a defined portion of the molecule and still result in a molecule with an acceptable level of equivalent immunological activity. An immunologically functional equivalent peptide or polypeptide is thus defined herein as those peptide(s) or polypeptide(s) in which certain, not most or all, of the amino acid(s) may be substituted.

In particular, where a shorter length peptide is concerned, it is contemplated that fewer amino acid substitutions should be made within the given peptide. A longer polypeptide may have an intermediate number of changes. The full length protein will have the most tolerance for a larger number of changes. Of course, a plurality of distinct polypeptides/peptides with different substitutions may easily be made and used in accordance with the invention.

It also is well understood that where certain residues are shown to be particularly important to the immunological or structural properties of a protein or peptide. This is an important consideration in the present invention, where changes in the toxin's immunogenic site(s) should be carefully considered and subsequently tested to ensure maintenance of immunological function (e.g., immunogenicity), where maintenance of immunological function is desired. In this manner, functional equivalents are defined herein as those peptides or polypeptides which maintain a substantial amount of their native immunological activity.

Amino acid substitutions are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues, glutamate and aspartate are negatively charged molecules; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as immunologically functional equivalents.

To effect more quantitative changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein, polypeptide or peptide is generally understood in the art (Kyte and Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

Numerous scientific publications have also been devoted to the prediction of secondary structure, and to the identification of an epitope, from analyses of an amino acid sequence (Chou and Fasman, 1974a,b; 1978a,b, 1979). Any of these may be used, if desired, to supplement the teachings of Kyte and Doolittle, 1982).

Moreover, computer programs are currently available to assist with predicting an immunogenic portion and an epitopic core region of one or more proteins, polypeptides or peptides. Examples include those programs based upon the Jameson-Wolf analysis (Jameson and Wolf, 1988; Wolf et al., 1988), the program PepPlot® (Brutlag et al., 1990; Weinberger et al., 1985), and other new programs for protein tertiary structure prediction (Fetrow and Bryant, 1993). Another commercially available software program capable of carrying out such analyses is MacVector (IBI, New Haven, Conn.).

In further embodiments, major immunogenic determinants of a peptide or polypeptide may be identified by an empirical approach in which portions of a nucleic acid encoding a peptide or polypeptide are expressed in a recombinant host, and the resulting peptide(s) or polypeptide(s) tested for their ability to elicit an immune response. For example, PCR™ can be used to prepare a range of peptides or polypeptides lacking successively longer fragments of the C-terminus of the amino acid sequence. The immunoactivity of each of these peptides or polypeptides is determined to identify those fragments or domains that are immunodominant. Further studies in which only a small number of amino acids is removed at each iteration then allows the location of the immunogenic determinant(s) of the peptide or polypeptide to be more precisely determined.

Another method for determining a major immunogenic determinant of a peptide or polypeptide is the SPOTs™ system (Genosys Biotechnologies, Inc., The Woodlands, Tex.). In this method, overlapping peptides are synthesized on a cellulose membrane, which, following synthesis and deprotection, is screened using a polyclonal or monoclonal antibody. An immunogenic determinant of the peptides or polypeptides which are initially identified can be further localized by performing subsequent syntheses of smaller peptides with larger overlaps, and by eventually replacing individual amino acids at each position along the immunoreactive sequence.

Once one or more such analyses are completed, an immunogenic composition, such as, for example, a peptide or a polypeptide is prepared that contains at least the essential features of one or more immunogenic determinants. An immunogenic composition is then employed in the generation of antisera against the composition, and preferably the immunogenic determinant(s).

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid. Nucleic acids encoding these immunogenic compositions also can be constructed and inserted into one or more expression vectors by standard methods (Sambrook et al., 1987), for example, using PCR™ cloning methodology.

In addition to the peptidyl compounds described herein, the inventors also contemplate that other sterically similar compounds may be formulated to mimic the key portions of the peptide or polypeptide structure or to interact specifically with, for example, an antibody. Such compounds, which may be termed peptidomimetics, may be used in the same manner as a peptide or polypeptide of the invention and hence are also immunologically functional equivalents.

Certain mimetics that mimic elements of protein secondary structure are described in Johnson et al. (1993). The underlying rationale behind the use of peptide mimetics is that the peptide backbone of proteins exists chiefly to orientate amino acid side chains in such a way as to facilitate molecular interactions, such as those of antibody and antigen. A peptide mimetic is thus designed to permit molecular interactions similar to the natural molecule.

5. Immunogen Mutagenesis

In particular embodiments, an immunogenic composition is mutated for purposes such as, for example, enhancing its immunogenicity, or producing or identifying a immunologically functional equivalent sequence. Methods of mutagenesis are well known to those of skill in the art (Sambrook et al., 1987).

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal. As used herein, the term "oligonucleotide directed mutagenesis procedure" is intended to refer to a process that involves the template-dependent extension of a primer molecule. The term template-dependent process refers to nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

In a preferred embodiment, site-directed mutagenesis is used. Site-directed mutagenesis is a technique useful in the preparation of an immunogenic composition (e.g., an toxin immunogen comprising peptide or polypeptide, or immunologically functional equivalent protein, polypeptide or peptide), through specific mutagenesis of the underlying DNA. In general, the technique of site-directed mutagenesis is well known in the art. The technique further provides a ready ability to prepare and test sequence variants, incorporating one or more of the foregoing considerations, by introducing one or more nucleotide sequence changes into the DNA. Site-directed mutagenesis allows the production of a mutant through the use of specific oligonucleotide sequence(s) which encode the DNA sequence of the desired mutation, as well as a sufficient number of adjacent nucleotides, to provide a primer sequence of sufficient size and sequence complexity to form a stable duplex on both sides of the position being mutated. Typically, a primer of about 17 to about 75 nucleotides in length is preferred, with about 10 to about 25 or more residues on both sides of the position being altered, while primers of about 17 to about 25 nucleotides in length being more preferred, with about 5 to 10 residues on both sides of the position being altered.

In general, site-directed mutagenesis is performed by first obtaining a single-stranded vector, or separating two strands of a double stranded vector which includes within its sequence a DNA sequence encoding the desired protein. As will be appreciated by one of ordinary skill in the art, the technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids are also routinely employed in site-directed mutagenesis, which eliminates the step of transferring the gene of interest from a phage to a plasmid.

The mutagenic primer is then annealed with the single-stranded DNA preparation, and subjected to DNA polymerizing enzymes such as, for example, E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected that include recombinant vectors bearing the mutated sequence arrangement.

Alternatively, a pair of primers may be annealed to two separate strands of a double stranded vector to simultaneously synthesize both corresponding complementary strands with the desired mutation(s) in a PCR™ reaction. A genetic selection scheme to enrich for clones incorporating the mutagenic oligonucleotide has been devised (Kunkel et al., 1987). Alternatively, the use of PCR™ with commercially available thermostable enzymes such as Taq polymerase may be used to incorporate a mutagenic oligonucleotide primer into an amplified DNA fragment that can then be cloned into an appropriate cloning or expression vector (Tomic et al., 1990; Upender et al., 1995). A PCR™ employing a thermostable ligase in addition to a thermostable polymerase also may be used to incorporate a phosphorylated mutagenic oligonucleotide into an amplified DNA fragment that may then be cloned into an appropriate cloning or expression vector (Michael 1994).

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

Additionally, one particularly useful mutagenesis technique is alanine scanning mutagenesis in which a number of residues are substituted individually with the amino acid alanine so that the effects of losing side-chain interactions can be determined, while minimizing the risk of large-scale perturbations in protein conformation (Cunningham et al., 1989).

6. Vectors

In order to effect replication, expression or mutagenesis of a nucleic acid, the nucleic acid may be delivered ("transfected") into at least one cell. The transfection of cells may be used, in certain embodiments, to recombinately produce one or more vaccine components for subsequent purification and preparation into a pharmaceutical vaccine. In other embodiments, the nucleic acid may be comprised as a genetic vaccine that is administered to an animal. In other embodiments, the nucleic acid is transfected into at least one cell and the cell administered to an animal as a cellular vaccine component. The nucleic acid may consist only of naked recombinant DNA, or may comprise, for example, additional materials to protect the nucleic acid and/or aid its targeting to specific cell types.

The term "vector" is used to refer to a carrier nucleic acid molecule into which a nucleic acid sequence can be inserted for introduction into at least one cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found.

Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1988 and Ausubel et al., 1994, both incorporated herein by reference).

The term "expression vector" refers to any type of genetic construct comprising a nucleic acid coding for a RNA and capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell.

The nucleic acid encoding the immunogenic composition or other vaccine component may be stably integrated into the genome of the cell, or may be stably maintained in the cell as a separate, episomal segment of DNA. Such nucleic acid segments or "episomes" encode sequences sufficient to permit maintenance and replication independent of or in synchronization with the host cell cycle. Vectors and expression vectors may contain nucleic acid sequences that serve other functions as well and are described infra. How the expression construct is delivered to at least one cell and where in the cell the nucleic acid remains is dependent on the type of expression construct employed.

a. Promoters and Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription of a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the transcriptional start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose (lac) and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al., 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB, http://www.epd.isb-sib.ch/) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

The identity of tissue-specific promoters or elements, as well as assays to characterize their activity, is well known to those of skill in the art. Nonlimiting examples of such regions include the human LIMK2 gene (Nomoto et al., 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki et al., 1998), D1A dopamine receptor gene (Lee et al., 1997), insulin-like growth factor II (Wu et al., 1997), and human platelet endothelial cell adhesion molecule-1 (Almendro et al., 1996).

b. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert in the correct frame. The exogenous translational control signals and initiation codons can be either natural or synthetic.

In certain embodiments of the invention, the use of internal ribosome entry site (IRES) elements are used to create multigene, or polycistronic, messages. IRES elements are able to bypass the ribosome scanning model of 5' methylated Cap-dependent translation and begin translation at internal sites (Pelletier and Sonenberg, 1988). IRES elements from two members of the picornavirus family (polio and encephalomyocarditis) have been described (Pelletier and Sonenberg, 1988), as well as an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

c. Multiple Cloning Sites

Vectors can include a multiple cloning site (MCS), which is a nucleic acid region that contains multiple restriction enzyme sites, any of which can be used in conjunction with standard recombinant technology to digest the vector (see, for example, Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using one or two restriction enzyme(s) that cuts within the MCS to enable exogenous sequences to be ligated to the vector. "Ligation" refers to the process of forming phosphodiester bonds between two nucleic acid fragments. Techniques involving restriction enzymes and ligation reactions are well known to those of skill in the art of recombinant technology.

d. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, Chandler et al., 1997, herein incorporated by reference.)

e. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments, a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that the terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences.

Terminators contemplated for use in the invention include any known terminator of transcription described herein or known to one of ordinary skill in the art, including, but not limited to, for example, the termination sequences of genes, such as, for example, the bovine growth hormone terminator, or viral termination sequences, such as, for example, the SV40 terminator. In certain embodiments, the termination signal may be a lack of transcribable or translatable sequence, such as due to a sequence truncation.

f. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal or the bovine growth hormone polyadenylation signal, convenient and known to function well in various target cells. Polyadenylation may increase the stability of the transcript or may facilitate cytoplasmic transport.

g. Origins of Replication

In order to propagate a vector in a host cell, it may contain one or more origins of replication sites (often termed "replicon"), which is a specific nucleic acid sequence at which replication is initiated. Alternatively, an autonomously replicating sequence (ARS) can be employed if the host cell is yeast.

h. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, methotrexate, mycophenolic acid, zeocin and histidinol are useful selectable markers. In addition to markers conferring a phenotype that allows for the discrimination of transformants based on the implementation of conditions, other types of markers including screenable markers such as green fluorescent protein (GFP), whose basis is colorimetric analysis, are also contemplated. Alternatively, screenable enzymes such as herpes simplex virus thymidine kinase (tk)

or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

i. Plasmid Vectors

In certain embodiments, a plasmid vector is contemplated for use to transform a host cell. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, *E. coli* is often transformed using derivatives of pBR322, a plasmid derived from an *E. coli* species. pBR322 contains genes for ampicillin and tetracycline resistance and thus provides easy means for identifying transformed cells. The pBR plasmid, or other microbial plasmid or phage must also contain, or be modified to contain, for example, promoters which can be used by the microbial organism for expression of the encoded sequences.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as, for example, *E. coli* LE392.

Further useful plasmid vectors include pIN vectors (Inouye et al., 1985); and pGEX vectors, for use in generating glutathione S-transferase (GST) soluble fusion proteins for later purification and separation by cleavage. Other suitable fusion proteins are those with β-galactosidase, ubiquitin, and the like.

Bacterial host cells, for example, *E. coli*, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally for between 2 and 24 h, the cells are collected by centrifugation and washed to remove residual media.

In certain embodiments, a toxoid of the present invention may comprise a leader peptide sequence to foster secretion from a host cell during expression. In general embodiments, a nucleic acid segment encoding a leader peptide sequence upstream and in reading frame with the coding sequence for a toxoid of the present invention is used in recombinant expression of a toxoid in a host cell. In certain aspects, a leader peptide sequence comprises a signal recognized by a host cell that directs the transport of an expressed toxoid through the outer membrane of a cell or into the bacterial periplasmic space. In aspects wherein the toxoid is transported into the extracellular medium, a toxoid may be readily purified from host cells. In some aspects, the leader sequences may be removed by enzymatic cleavage. Such leader peptide sequences and nucleic acids encoding such are known in the art, and non-limiting examples include the secretory leader sequences of *E. coli* alkaline phosphatase (PhoA), immunoglobulins, LamB, MalE, outer membrane proteins (OmpA), PelB, penicillinase, StII, T-cell receptors, Lpp, and the like.

In general embodiments, nucleic acids and/or expressed proteins, polypeptide or peptide can be purified by methods well known to those of skill in the art (see, for example, Sambrook et al, 1989, incorporated herein by reference).

j. Viral Vectors

The ability of certain viruses to infect cells or enter cells via receptor-mediated endocytosis, and to integrate into host cell genome and express viral genes stably and efficiently have made them attractive candidates for the transfer of foreign nucleic acids into cells (e.g., mammalian cells). One or more vaccine component of the present invention may be a viral vector that encodes one or more immunogenic compositions or other components such as, for example, an immunomodulator or adjuvant. Non-limiting examples of virus vectors that may be used to deliver a nucleic acid of the present invention are described below.

1. Adenoviral Vectors

A particular method for delivery of the nucleic acid involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue or cell-specific construct that has been cloned therein. Knowledge of the genetic organization or adenovirus, a 36 kb, linear, double-stranded DNA virus, allows substitution of large pieces of adenoviral DNA with foreign sequences up to 7 kb (Grunhaus and Horwitz, 1992).

2. AAV Vectors

The nucleic acid may be introduced into the cell using adenovirus-assisted transfection. Increased transfection efficiencies have been reported in cell systems using adenovirus coupled systems (Kelleher and Vos, 1994; Cotten et al., 1992; Curiel, 1994). Adeno-associated virus (AAV) is an attractive vector system for use in the vaccines of the present invention as it has a high frequency of integration and it can infect nondividing cells, thus making it useful for delivery of genes into mammalian cells, for example, in tissue culture (Muzyczka, 1992) or in vivo. AAV has a broad host range for infectivity (Tratschin et al., 1984; Laughlin et al., 1986; Lebkowski et al., 1988; McLaughlin et al., 1988). Details concerning the generation and use of rAAV vectors are described in U.S. Pat. Nos. 5,139,941 and 4,797,368, each incorporated herein by reference.

3. Retroviral Vectors

Retroviruses have promise as antigen delivery vectors in vaccines due to their ability to integrate their genes into the host genome, transferring a large amount of foreign genetic material, infecting a broad spectrum of species and cell types, and of being packaged in special cell-lines (Miller, 1992).

In order to construct a vaccine retroviral vector, a nucleic acid (e.g., one encoding an immunogen of interest) is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences, is introduced into a special cell line (e.g., by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Lentiviruses are complex retroviruses which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136). Some examples of lentivirus include the Human Immunodeficiency Viruses, HIV-1, HIV-2, and the Simian Immunodeficiency Virus, SIV. Lentiviral vectors have been generated by multiply attenuating the HIV virulence genes, for example, the genes env, vif, vpr, vpu and nef are deleted, making the vector biologically safe.

Recombinant lentiviral vectors can be made capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

4. Other Viral Vectors

Other viral vectors may be employed as vaccine constructs in the present invention. Vectors derived from viruses such as vaccinia virus (Ridgeway, 1988; Baichwal and Sugden, 1986; Coupar et al., 1988), sindbis virus, cytomegalovirus, and herpes simplex virus may be employed. They offer several attractive features for various mammalian cells (Friedmann, 1989; Ridgeway, 1988; Baichwal and Sugden, 1986; Coupar et al., 1988; Horwich et al., 1990).

5. Vaccine Delivery Using Modified Viruses

A nucleic acid to be delivered may be housed within an infective virus that has been engineered to express a specific binding ligand. The virus particle will thus bind specifically to the cognate receptors of the target cell and deliver the contents to the cell. A novel approach designed to allow specific targeting of retrovirus vectors was recently developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989). Thus, it is contemplated that antibodies, specific binding ligands and/or other targeting moieties may be used to specifically transfect APC types.

7. Vector Delivery and Cell Transformation

Suitable methods for nucleic acid delivery for transformation of an organelle, a cell, a tissue or an organism for use with the current invention are believed to include virtually any method by which a nucleic acid (e.g., DNA) can be introduced into an organelle, a cell, a tissue or an organism, as described herein or as would be known to one of ordinary skill in the art. Such methods include, but are not limited to, direct delivery of DNA such as by injection (U.S. Pat. Nos. 5,994, 624, 5,981,274, 5,945,100, 5,780,448, 5,736,524, 5,702,932, 5,656,610, 5,589,466 and 5,580,859, each incorporated herein by reference), including microinjection (Harlan and Weintraub, 1985; U.S. Pat. No. 5,789,215, incorporated herein by reference); by electroporation (U.S. Pat. No. 5,384, 253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610, 042; 5,322,783 5,563,055, 5,550,318, 5,538,877 and 5,538, 880, and each incorporated herein by reference); by agitation with silicon carbide fibers (Kaeppler et al., 1990; U.S. Pat. Nos. 5,302,523 and 5,464,765, each incorporated herein by reference); by Agrobacterium-mediated transformation (U.S. Pat. Nos. 5,591,616 and 5,563,055, each incorporated herein by reference); by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985), and any combination of such methods. Through the application of techniques such as these, organelle(s), cell(s), tissue(s) or organism(s) may be stably or transiently transformed.

8. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to at least one cell into which an exogenous nucleic acid sequence, such as, for example, a vector, has been introduced. Therefore, recombinant cells are distinguishable from naturally occurring cells which do not contain a recombinantly introduced nucleic acid.

In certain embodiments, it is contemplated that RNAs or proteinaceous sequences may be co-expressed with other selected RNAs or proteinaceous sequences in the same host cell. Co-expression may be achieved by co-transfecting the host cell with two or more distinct recombinant vectors. Alternatively, a single recombinant vector may be constructed to include multiple distinct coding regions for RNAs, which could then be expressed in host cells transfected with the single vector.

A tissue may comprise a host cell or cells to be transformed with a nucleic acid encoding a vaccine component. The tissue may be part or separated from an organism. In certain embodiments, a tissue may comprise, but is not limited to, adipocytes, alveolar, ameloblasts, axon, basal cells, blood (e.g., lymphocytes), blood vessel, bone, bone marrow, brain, breast, cartilage, cervix, colon, cornea, embryonic, endometrium, endothelial, epithelial, esophagus, facia, fibroblast, follicular, ganglion cells, glial cells, goblet cells, kidney, liver, lung, lymph node, muscle, neuron, ovaries, pancreas, peripheral blood, prostate, skin, small intestine, spleen, stem cells, stomach, testes, anthers, ascite tissue, cobs, ears, flowers, husks, kernels, leaves, meristematic cells, pollen, root tips, roots, silk, stalks, and all cancers thereof.

In certain embodiments, the host cell or tissue may be comprised in at least one organism. In certain embodiments, the organism may be, but is not limited to, a prokayote (e.g., a eubacteria, an archaea) or an eukaryote, as would be understood by one of ordinary skill in the art (see, for example, webpage http://phylogeny.arizona.edu/tree/phylogeny.html).

Numerous cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryote host cell for replication of many vectors. Cell types available for vector replication and/or expression include, but are not limited to, bacteria, such as *E. coli* (e.g., *E. coli* strain RR1, *E. coli* LE392, *E. coli* B, *E. coli* X 1776 (ATCC No. 31537) as well as *E. coli* W3110 (F-, lambda-, prototrophic, ATCC No. 273325), DH5α, JM109, and KCB, bacilli such as *Bacillus subtilis*; and other enterobacteriaceae such as *Salmonella typhimurium, Serratia marcescens*, various *Pseudomonas* species, as well as a number of commercially available bacterial hosts such as SURE® Competent Cells and SOLOPACK™ Gold Cells (STRATAGENE®, La Jolla). In certain embodiments, bacterial cells such as *E. coli* LE392 are particularly contemplated as host cells for phage viruses.

Examples of eukaryotic host cells for replication and/or expression of a vector include, but are not limited to, HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector. In certain embodiments, expression of toxins is preferred in prokaryotic cells, as enzymatically active toxins may kill a eukaryotic host.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

9. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

Other examples of expression systems include STRATAGEN®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

It is contemplated that the proteins, polypeptides or peptides produced by the methods of the invention may be "overexpressed", i.e., expressed in increased levels relative to its natural expression in cells. Such overexpression may be assessed by a variety of methods, including radio-labeling and/or protein purification. However, simple and direct methods are preferred, for example, those involving SDS/PAGE and protein staining or western blotting, followed by quantitative analyses, such as densitometric scanning of the resultant gel or blot. A specific increase in the level of the recombinant protein, polypeptide or peptide in comparison to the level in natural cells is indicative of overexpression, as is a relative abundance of the specific protein, polypeptides or peptides in relation to the other proteins produced by the host cell and, e.g., visible on a gel.

In some embodiments, the expressed proteinaceous sequence forms an inclusion body in the host cell. The host cells are lysed, for example, by disruption in a cell homogenizer, washed and/or centrifuged to separate the dense inclusion bodies and cell membranes from the soluble cell components. This centrifugation can be performed under conditions whereby the dense inclusion bodies are selectively enriched by incorporation of sugars, such as sucrose, into the buffer and centrifugation at a selective speed. Inclusion bodies may be solubilized in solutions containing high concentrations of urea (e.g. 8M) or chaotropic agents such as guanidine hydrochloride in the presence of reducing agents, such as β-mercaptoethanol or DTT (dithiothreitol), and refolded into a more desirable conformation, as would be known to one of ordinary skill in the art.

10. Additional Vaccine Components

It is contemplated that an immunogenic composition of the invention may be combined with one or more additional components to form a more effective vaccine. Non-limiting examples of additional components include, for example, one or more additional immunogens, immunomodulators or adjuvants to stimulate an immune response to an immunogenic composition of the present invention and/or the additional component(s).

a. Immunomodulators

For example, it is contemplated that immunomodulators can be included in the vaccine to augment a cell's or a patient's (e.g., a human's) response. Immunomodulators can be included as purified proteins, nucleic acids encoding immunomodulators, and/or cells that express immunomodulators in the vaccine composition. The following sections list non-limiting examples of immunomodulators that are of interest, and it is contemplated that various combinations of immunomodulators may be used in certain embodiments (e.g., a cytokine and a chemokine).

i. Cytokines

Interleukins, cytokines, nucleic acids encoding interleukins or cytokines, and/or cells expressing such compounds are contemplated as possible vaccine components. Interleukins and cytokines, include but are not limited to interleukin 1 (IL-1), IL-2, IL-3, IL-4, IL-5, IL-6, IL-7, IL-8, IL-9, IL-10, IL-11, IL-12, IL-13, IL-14, IL-15, IL-18, β-interferon, α-interferon, γ-interferon, angiostatin, thrombospondin, endostatin, GM-CSF, G-CSF, M-CSF, METH-1, METH-2, tumor necrosis factor, TGFβ, LT and combinations thereof.

ii. Chemokines

Chemokines, nucleic acids that encode for chemokines, and/or cells that express such also may be used as vaccine components. Chemokines generally act as chemoattractants to recruit immune effector cells to the site of chemokine expression. It may be advantageous to express a particular chemokine coding sequence in combination with, for example, a cytokine coding sequence, to enhance the recruitment of other immune system components to the site of treatment. Such chemokines include, for example, RANTES, MCAF, MIP1-alpha, MIP1-Beta, IP-10 and combinations thereof. The skilled artisan will recognize that certain cytokines are also known to have chemoattractant effects and could also be classified under the term chemokines.

iii. Immunogenic Carrier Proteins

In certain embodiments, an immunogenic composition may be chemically coupled to a carrier or recombinantly expressed with a immunogenic carrier peptide or polypeptide (e.g., an antigen-carrier fusion peptide or polypeptide) to enhance an immune reaction. Exemplary and preferred immunogenic carrier amino acid sequences include hepatitis B surface antigen, keyhole limpet hemocyanin (KLH) and bovine serum albumin (BSA). Other albumins such as ovalbumin, mouse serum albumin or rabbit serum albumin also can be used as immunogenic carrier proteins. Means for conjugating a polypeptide or peptide to a immunogenic carrier protein are well known in the art and include, for example, glutaraldehyde, m-maleimidobenzoyl-N-hydroxysuccinimide ester, carbodiimide and bis-biazotized benzidine.

iv. Biological Response Modifiers

It may be desirable to coadminister biologic response modifiers (BRM), which have been shown to upregulate T cell immunity or downregulate suppressor cell activity. Such BRMs include, but are not limited to, cimetidine (CIM; 1200 mg/d) (Smith/Kline, PA); low-dose cyclophosphamide (CYP; 300 mg/m$^2$) (Johnson/Mead, NJ), or a gene encoding a protein involved in one or more immune helper functions, such as B-7.

b. Adjuvants

Immunization protocols have used adjuvants to stimulate responses for many years, and as such adjuvants are well known to one of ordinary skill in the art. Some adjuvants affect the way in which immunogens are presented. For example, the immune response is increased when protein immunogens are precipitated by alum. Emulsification of immunogens also prolongs the duration of immunogen presentation.

In one aspect, an adjuvant effect is achieved by use of an agent, such as alum, used in about 0.05 to about 0.1% solution in phosphate buffered saline. Alternatively, the immunogen is made as an admixture with synthetic polymers of sugars (Carbopol®) used as an about 0.25% solution. Adjuvant effect may also be made by aggregation of the immunogen in the vaccine by heat treatment with temperatures ranging between about 70° to about 101° C. for a 30-second to 2-minute period. Aggregation by reactivating with pepsin-treated (Fab) antibodies to albumin, mixture with bacterial cell(s) such as C. parvum or an endotoxin or lipopolysaccharide components of Gram-negative bacteria, emulsion in physiologically acceptable oil vehicles, such as mannide mono-oleate (Aracel A) or emulsion with a 20% solution of a perfluorocarbon (Fluosol-DA®) used as a block substitute, also may be employed.

Some adjuvants, for example, certain organic molecules obtained from bacteria, act on the host rather than on the immunogen. An example is muramyl dipeptide (N-acetylmuramyl-L-alanyl-D-isoglutamine [MDP]), a bacterial peptidoglycan. Derivatives of muramyl dipeptide, such as the amino acid derivative threonyl-MDP, and the fatty acid derivative MTPPE, are also contemplated. The effects of MDP, as with most adjuvants, are not fully understood. MDP stimulates macrophages but also appears to stimulate B cells directly. The effects of adjuvants, therefore, are not immunogen-specific. If they are administered together with a purified immunogen, however, they can be used to selectively promote the response to the immunogen.

U.S. Pat. No. 4,950,645 describes a lipophilic disaccharide-tripeptide derivative of muramyl dipeptide which is described for use in artificial liposomes formed from phosphatidyl choline and phosphatidyl glycerol. It is thought to be effective in activating human monocytes and destroying tumor cells, but is non-toxic in generally high doses. The compounds of U.S. Pat. No. 4,950,645 and PCT Patent Application WO 91/16347, are contemplated for use with cellular carriers and other embodiments of the present invention.

Adjuvants have been used experimentally to promote a generalized increase in immunity against unknown immunogens (e.g., U.S. Pat. No. 4,877,611). In certain embodiments, hemocyanins and hemoerythrins may also be used in the invention. The use of hemocyanin from keyhole limpet (KLH) is preferred in certain embodiments, although other molluscan and arthropod hemocyanins and hemoerythrins may be employed.

Various polysaccharide adjuvants may also be used. For example, the effect of various pneumococcal polysaccharide adjuvants on the antibody response of mice has been described (Yin et al., 1989). The doses that produce optimal responses, or that otherwise do not produce suppression, should be employed as indicated (Yin et al., 1989). Polyamine varieties of polysaccharides are particularly preferred, such as chitin and chitosan, including deacetylated chitin.

Another adjuvant contemplated for use in the present invention is BCG. BCG (bacillus Calmette-Guerin, an attenuated strain of Mycobacterium) and BCG-cell wall skeleton (CWS) may also be used as adjuvants in the invention, with or without trehalose dimycolate. Trehalose dimycolate may be used itself. Trehalose dimycolate administration has been shown to correlate with augmented resistance to influenza virus infection in mice (Azuma et al., 1988). Trehalose dimycolate may be prepared as described in U.S. Pat. No. 4,579,945.

BCG is an important clinical tool because of its immunostimulatory properties. BCG acts to stimulate the reticuloendothelial system, activates natural killer cells and increases proliferation of hematopoietic stem cells. Cell wall extracts of BCG have proven to have excellent immune adjuvant activity. Molecular genetic tools and methods for mycobacteria have provided the means to introduce foreign genes into BCG (Jacobs et al., 1987; Snapper et al., 1988; Husson et al., 1990; Martin et al., 1990).

Live BCG is an effective and safe vaccine used worldwide to prevent tuberculosis. BCG and other mycobacteria are highly effective adjuvants, and the immune response to mycobacteria has been studied extensively. With nearly 2 billion immunizations, BCG has a long record of safe use in man (Luelmo, 1982; Lotte et al., 1984). It is one of the few vaccines that can be given at birth, it engenders long-lived immune responses with only a single dose, and there is a worldwide distribution network with experience in BCG vaccination. An exemplary BCG vaccine is sold as TICE® BCG (Organon Inc., West Orange, N.J.).

In a typical practice of the present invention, cells of *Mycobacterium bovis*-BCG are grown and harvested by methods known in the art. For example, they may be grown as a surface pellicle on a Sauton medium or in a fermentation vessel containing the dispersed culture in a Dubos medium (Dubos et al., 1947; Rosenthal, 1937). All the cultures are harvested after 14 days incubation at about 37° C. Cells grown as a pellicle are harvested by using a platinum loop whereas those from the fermenter are harvested by centrifugation or tangential-flow filtration. The harvested cells are resuspended in an aqueous sterile buffer medium. A typical suspension contains from about $2\times10^{10}$ cells/ml to about $2\times10^{12}$ cells/ml. To this bacterial suspension, a sterile solution containing a selected enzyme which will degrade the BCG cell covering material is added. The resultant suspension is agitated such as by stirring to ensure maximal dispersal of the BCG organisms. Thereafter, a more concentrated cell suspension is prepared and the enzyme in the concentrate removed, typically by washing with an aqueous buffer, employing known techniques such as tangential-flow filtration. The enzyme-free cells are adjusted to an optimal immunological concentration with a cryoprotectant solution, after which they are filled into vials, ampoules, etc., and lyophilized, yielding BCG vaccine, which upon reconstitution with water is ready for immunization.

Amphipathic and surface active agents, e.g., saponin and derivatives such as QS21 (Cambridge Biotech), form yet another group of adjuvants for use with the immunogens of the present invention. Nonionic block copolymer surfactants (Rabinovich et al., 1994; Hunter et al., 1991) may also be employed. Oligonucleotides are another useful group of adjuvants (Yamamoto et al., 1988). Quil A and lentinen are other adjuvants that may be used in certain embodiments of the present invention.

One group of adjuvants preferred for use in the invention are the detoxified endotoxins, such as the refined detoxified endotoxin of U.S. Pat. No. 4,866,034. These refined detoxified endotoxins are effective in producing adjuvant responses in mammals. Of course, the detoxified endotoxins may be combined with other adjuvants to prepare multi-adjuvant-incorporated cells. For example, combination of detoxified endotoxins with trehalose dimycolate is particularly contemplated, as described in U.S. Pat. No. 4,435,386. Combinations of detoxified endotoxins with trehalose dimycolate and endotoxic glycolipids is also contemplated (U.S. Pat. No. 4,505,899), as is combination of detoxified endotoxins with cell wall skeleton (CWS) or CWS and trehalose dimycolate, as described in U.S. Pat. Nos. 4,436,727, 4,436,728 and 4,505,900. Combinations of just CWS and trehalose dimycolate, without detoxified endotoxins, is also envisioned to be useful, as described in U.S. Pat. No. 4,520,019.

In other embodiments, the present invention contemplates that a variety of adjuvants may be employed in the membranes of cells, resulting in an improved immunogenic composition. The only requirement is, generally, that the adjuvant be capable of incorporation into, physical association with, or conjugation to, the cell membrane of the cell in question. Those of skill in the art will know the different kinds of adjuvants that can be conjugated to cellular vaccines in accordance with this invention and these include alkyl lysophospholipids (ALP); BCG; and biotin (including biotinylated derivatives) among others. Certain adjuvants particularly contemplated for use are the teichoic acids from Gram negative cells. These include the lipoteichoic acids (LTA), ribitol teichoic acids (RTA) and glycerol teichoic acid (GTA). Active forms of their synthetic counterparts may also be employed in connection with the invention (Takada et al., 1995a).

Various adjuvants, even those that are not commonly used in humans, may still be employed in animals, where, for example, one desires to raise antibodies or to subsequently obtain activated T cells. The toxicity or other adverse effects that may result from either the adjuvant or the cells, e.g., as may occur using non-irradiated tumor cells, is irrelevant in such circumstances.

One group of adjuvants preferred for use in some embodiments of the present invention are those that can be encoded by a nucleic acid (e.g., DNA or RNA). It is contemplated that such adjuvants may be encoded in a nucleic acid (e.g., an expression vector) encoding the immunogen, or in a separate vector or other construct. These nucleic acids encoding the adjuvants can be delivered directly, such as for example with lipids or liposomes.

c. Excipients, Salts and Auxiliary Substances

An immunogenic composition of the present invention may be mixed with one or more additional components (e.g., excipients, salts, etc.) which are pharmaceutically acceptable and compatible with at least one active ingredient (e.g., immunogen). Suitable excipients are, for example, water, saline, dextrose, glycerol, ethanol and combinations thereof.

In addition, if desired, an immunogenic composition may comprise minor amounts of one or more auxiliary substances such as for example wetting or emulsifying agents, pH buffering agents, etc. which enhance the effectiveness of the immunogenic composition or vaccine.

11. Vaccine Component Purification

In any case, a vaccine component (e.g., an immunogenic peptide or polypeptide or nucleic acid encoding a proteinaceous composition) may be isolated and/or purified from the chemical synthesis reagents, cell or cellular components. In a method of producing the vaccine component, purification is accomplished by any appropriate technique that is described herein or well-known to those of skill in the art (e.g., Sambrook et al., 1987). Although preferred for use in certain embodiments, there is no general requirement that an immunogenic composition of the present invention or other vaccine component always be provided in their most purified state. Indeed, it is contemplated that a less substantially purified vaccine component, which is nonetheless enriched in the desired compound, relative to the natural state, will have utility in certain embodiments, such as, for example, total recovery of protein product, or in maintaining the activity of an expressed protein. However, it is contemplated that inactive products also have utility in certain embodiments, such as, e.g., in determining immunogenicity via antibody generation.

The present invention also provides purified, and in preferred embodiments, substantially purified vaccines or vaccine components. The term “purified vaccine component” as used herein, is intended to refer to at least one vaccine component (e.g., a proteinaceous composition, isolatable from cells), wherein the component is purified to any degree relative to its naturally-obtainable state, e.g., relative to its purity within a cellular extract or reagents of chemical synthesis. In certain aspects wherein the vaccine component is a proteinaceous composition, a purified vaccine component also refers to a wild-type or mutant protein, polypeptide, or peptide free from the environment in which it naturally occurs.

Where the term "substantially purified" is used, this will refer to a composition in which the specific compound (e.g., a protein, polypeptide, or peptide) forms the major component of the composition, such as constituting about 50% of the compounds in the composition or more. In preferred embodiments, a substantially purified vaccine component will constitute more than about 60%, about 70%, about 80%, about 90%, about 95%, about 99% or even more of the compounds in the composition.

In certain embodiments, a vaccine component may be purified to homogeneity. As applied to the present invention, "purified to homogeneity," means that the vaccine component has a level of purity where the compound is substantially free from other chemicals, biomolecules or cells. For example, a purified peptide, polypeptide or protein will often be sufficiently free of other protein components so that degradative sequencing may be performed successfully. Various methods for quantifying the degree of purification of a vaccine component will be known to those of skill in the art in light of the present disclosure. These include, for example, determining the specific protein activity of a fraction (e.g., immunogenicity), or assessing the number of polypeptides within a fraction by gel electrophoresis.

Various techniques suitable for use in chemical, biomolecule or biological purification, well known to those of skill in the art, may be applicable to preparation of a vaccine component of the present invention. These include, for example, precipitation with ammonium sulfate, PEG, antibodies and the like or by heat denaturation, followed by centrifugation; fractionation, chromatographic procedures, including but not limited to, partition chromatograph (e.g., paper chromatograph, thin-layer chromatograph (TLC), gas-liquid chromatography and gel chromatography) gas chromatography, high performance liquid chromatography, affinity chromatography, supercritical flow chromatography, ion exchange chromatography, gel filtration chromatography, reverse phase chromatography, hydroxylapatite chromatography, lectin affinity chromatography; isoelectric focusing and gel electrophoresis (see for example, Sambrook et al. 1989; and Freifelder, Physical Biochemistry, Second Edition, pages 238-246, incorporated herein by reference).

Given that many DNA and proteins are known (see for example, the National Center for Biotechnology Information's Genbank and GenPept databases (http://www.ncbi.nlm.nih.gov/)), or may be identified and amplified using the methods described herein, any purification method for recombinately expressed nucleic acid or proteinaceous sequences known to those of skill in the art can now be employed. In certain aspects, a nucleic acid may be purified on polyacrylamide gels, and/or cesium chloride centrifugation gradients, or by any other means known to one of ordinary skill in the art (see for example, Sambrook et al. 1989, incorporated herein by reference). In further aspects, a purification of a proteinaceous sequence may be conducted by recombinately expressing the sequence as a fusion protein. Such purification methods are routine in the art. This is exemplified by the generation of an specific protein-glutathione S-transferase fusion protein, expression in *E. coli*, and isolation to homogeneity using affinity chromatography on glutathione-agarose, or the generation of a polyhistidine tag on the N- or C-terminus of the protein, and subsequent purification using Ni-affinity chromatography. In particular aspects, cells or other components of the vaccine may be purified by flow cytometry. Flow cytometry involves the separation of cells or other particles in a liquid sample, and is well known in the art (see, for example, U.S. Pat. Nos. 3,826,364, 4,284, 412, 4,989,977, 4,498,766, 5,478,722, 4,857,451, 4,774,189, 4,767,206, 4,714,682, 5,160,974 and 4,661,913). Any of these techniques described herein, and combinations of these and any other techniques known to skilled artisans, may be used to purify and/or assay the purity of the various chemicals, proteinaceous compounds, nucleic acids, cellular materials and/or cells that may comprise a vaccine of the present invention. As is generally known in the art, it is believed that the order of conducting the various purification steps may be changed, or that certain steps may be omitted, and still result in a suitable method for the preparation of a substantially purified immunogen or other vaccine component.

12. Vaccine Preparations

Once produced, synthesized and/or purified, an immunogen or other vaccine component may be prepared as a vaccine for administration to a patient. The preparation of a vaccine is generally well understood in the art, as exemplified by U.S. Pat. Nos. 4,608,251, 4,601,903, 4,599,231, 4,599,230, and 4,596,792, all incorporated herein by reference. Such methods may be used to prepare a vaccine comprising an immunogenic composition comprising at least one toxoid as active ingredient(s), in light of the present disclosure. In preferred embodiments, the compositions of the present invention are prepared to be pharmacologically acceptable vaccines.

Pharmaceutical vaccine compositions of the present invention comprise an effective amount of one or more toxoids or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one toxoid or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). The vaccine components of the present invention may comprise different types of carriers depending on whether it is to be administered in solid, liquid or aerosol form, and whether it needs to be sterile for such routes of administration as injection. Except insofar as any conventional carrier is incompatible with the active ingredient, its use in the therapeutic or pharmaceutical compositions is contemplated.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The vaccine component(s) may be formulated into a composition in a free base, neutral or salt form. Pharmaceutically acceptable salts, include the acid addition salts, e.g., those formed with the free amino groups of a proteinaceous composition, or which are formed with inorganic acids such as, for example, hydrochloric or phosphoric acids, or such organic acids as acetic, oxalic, tartaric or mandelic acid. Salts formed with the free carboxyl groups can also be derived from inorganic bases such as, for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example, liquid polyol or lipids; by the use of surfactants such as, for example, hydroxypropylcellulose; or combinations thereof. In many cases, it will be preferable to include isotonic agents, such as, for example, sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the vaccine component(s) are prepared for administration by such routes as oral ingestion. In these embodiments, the composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc., or combinations thereof. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations which are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various of the other ingredients enumerated above, as required, followed by filter sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously filter-sterilized liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

13. Vaccine Administration

The manner of administration of a vaccine may be varied widely. Any of the conventional methods for administration of a vaccine are applicable. For example, a vaccine may be conventionally administered intravenously, intradermally, intraarterially, intraperitoneally, intralesionally, intracranially, intraarticularly, intraprostatically, intrapleurally, intratracheally, intranasally, intravitreally, intravaginally, intratumorally, intramuscularly, subcutaneously, intravesicularlly, mucosally, intrapericardially, orally, rectally, nasally, topically, in eye drops, locally, using aerosol, injection, infusion, continuous infusion, localized perfusion, bathing target cells directly, via a catheter, via a lavage, in creams, in lipid compositions (e.g., liposomes), or by other methods or any combination of the forgoing as would be known to one of ordinary skill in the art (see, for example, Remington's Pharmaceutical Sciences, 18th Ed. Mack Printing Company, 1990, incorporated herein by reference).

A vaccination schedule and dosages may be varied on a patient by patient basis, taking into account, for example, factors such as the weight and age of the patient, the type of disease being treated, the severity of the disease condition, previous or concurrent therapeutic interventions, the manner of administration and the like, which can be readily determined by one of ordinary skill in the art.

A vaccine is administered in a manner compatible with the dosage formulation, and in such amount as will be therapeutically effective and immunogenic. For example, the intramuscular route may be preferred in the case of toxins with short half lives in vivo. The quantity to be administered depends on the subject to be treated, including, e.g., the capacity of the individual's immune system to mount an immune response, and the degree of protection desired. The dosage of the vaccine will depend on the route of administration and will vary according to the size of the subject. Precise amounts of an active ingredient required to be administered depend on the judgment of the practitioner. In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. However, a suitable dosage range may be, for example, of the order of several hundred micrograms active ingredient per vaccination. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per vaccination, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above. A suitable regime for initial administration and booster administrations (e.g., innoculations) are also variable, but are typified by an initial administration followed by subsequent inoculation(s) or other administration(s).

In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1-5 years, usually three years, will be desirable to maintain protective levels of the antibodies.

The course of the immunization may be followed by assays for antibodies for the supernatant antigens. The assays may be performed by labeling with conventional labels, such as radionuclides, enzymes, fluorescents, and the like. These techniques are well known and may be found in a wide variety of patents, such as U.S. Pat. Nos. 3,791,932; 4,174,384 and 3,949,064, as illustrative of these types of assays. Other immune assays can be performed and assays of protection from challenge with the wild-type sequences can be performed in non-humans, following immunization.

14. Enhancement of an Immune Response

The present invention includes a method of enhancing the immune response in a subject comprising the steps of contacting one or more lymphocytes with an immunogenic composition, wherein the immunogen comprises as part of its sequence a sequence in accordance with SEQ ID NO:1, or a immunologically functional equivalent thereof. In certain embodiments the one or more lymphocytes is comprised in an animal, such as a human. In other embodiments, the lymphocyte(s) may be isolated from an animal or from a tissue (e.g., blood) of the animal. In certain preferred embodiments, the lymphocyte(s) are peripheral blood lymphocyte(s). In certain embodiments, the one or more lymphocytes comprise a T-lymphocyte or a B-lymphocyte. In a particularly preferred facet, the T-lymphocyte is a cytotoxic T-lymphocyte.

The enhanced immune response may be an active or a passive immune response. Alternatively, the response may be part of an adoptive immunotherapy approach in which lymphocyte(s) are obtained from an animal (e.g., a patient), then pulsed with composition comprising an immunogenic composition. In a preferred embodiment, the lymphocyte(s) may be be administered to the same or different animal (e.g., same or different donors).

a. Cytotoxic T Lymphocytes

In certain embodiments, T-lymphocytes are specifically activated by contact with an immunogenic composition of the present invention. In certain embodiments, T-lymphocytes are activated by contact with an antigen presenting cell that is or has been in contact with an immunogenic composition of the invention.

T cells express a unique antigen binding receptor on their membrane (T-cell receptor), which can only recognize antigen in association with major histocompatibility complex (MHC) molecules on the surface of other cells. There are several populations of T cells, such as T helper cells and T cytotoxic cells. T helper cells and T cytotoxic cells are primarily distinguished by their display of the membrane bound glycoproteins CD4 and CD8, respectively. T helper cells secret various lymphokines, that are crucial for the activation of B cells, T cytotoxic cells, macrophages and other cells of the immune system. In contrast, a T cytotoxic cell that recognizes an antigen-MHC complex proliferates and differentiates into an effector cell called a cytotoxic T lymphocyte (CTL). CTLs eliminate cells of the body displaying antigen by producing substances that result in cell lysis.

In certain aspects, T helper cell responses can be measured by an in vitro or in vivo assay with peptides, polypeptides or proteins. In vitro assays include measurement of a specific cytokine release by enzyme, radioisotope, chromaphore or fluorescent assays. In vivo assays include delayed type hypersensitivity responses called skin tests, as would be known to one of ordinary skill in the art.

b. Antigen Presenting Cells

In general, the term "antigen presenting cell" can be any cell that accomplishes the goal of the invention by aiding the enhancement of an immune response (i.e., from the T-cell or B-cell arms of the immune system) against an immunogen (e.g., an immunogenic toxin or a immunologically functional equivalent) or immunogenic composition of the present invention. Such cells can be defined by those of skill in the art, using methods disclosed herein and in the art. As is understood by one of ordinary skill in the art (see for example Kuby, 1993, incorporated herein by reference), and used here in certain embodiments, at least one cell that displays or presents an antigen normally or preferentially with a class II major histocompatability molecule or complex to an immune cell is an "antigen presenting cell." In certain aspects, at least one cell (e.g., an APC cell) may be fused with another cell, such as a recombinant cell or a tumor cell that expresses the desired immunogen. Methods for preparing a fusion of two or more cells are well known in the art, such as for example, the methods disclosed in Goding, pp. 65-66, 71-74 1986; Campbell, pp. 75-83, 1984; Kohler and Milstein, 1975; Kohler and Milstein, 1976; Gefter et al., 1977, each incorporated herein by reference. In some cases, the immune cell to which an antigen presenting cell displays or presents an antigen to is a CD4 positive T-helper (CD4$^+$T$_H$)cell. Additional molecules expressed on the APC or other immune cells may aid or improve the enhancement of an immune response. Secreted or soluble molecules, such as, for example, immunomodulators and adjuvants, may also aid or enhance the immune response against an immunogen. Such molecules are well known to one of skill in the art, and various examples are described herein.

15. Antibody Generation

In certain embodiments, isolated antibodies to the immunogenic compositions of the present invention are contemplated as useful for purification, diagnostic and therapeutic applications. Monoclonal antibodies (MAbs) are recognized to have certain advantages, e.g., reproducibility and large-scale production, and their use is generally preferred. MAbs may be readily prepared through use of well-known techniques, such as those exemplified in U.S. Pat. No. 4,196,265, incorporated herein by reference.

In certain diagnostic or vaccine component purification aspects, an antibody specific to one or more vaccine components, such as an immunogenic toxin, may be used. Non-limiting examples of such immunodetection methods include enzyme linked immunosorbent assay (ELISA), radioimmunoassay (RIA), immunoradiometric assay, fluoroimmunoassay, chemiluminescent assay, bioluminescent assay, and Western blot, to mention a few. The steps of various useful immunodetection methods have been described in the scientific literature, such as, e.g., Doolittle M H and Ben-Zeev O, 1999; Gulbis B and Galand P, 1993; De Jager R et al., 1993; and Nakamura et al., 1987, each incorporated herein by reference. Often, the antibody may be conjugated with an imaging agent to enhance detection of a vaccine component ligand bound to the antibody, as would be known to one of ordinary skill in the art. Many appropriate imaging agents are known in the art, as are methods for their attachment to antibodies (see, for e.g., U.S. Pat. Nos. 5,021,236; 4,938,948; and 4,472,509, each incorporated herein by reference).

In general, the detection of immunocomplex formation is well known in the art and may be achieved through the application of numerous approaches. These methods are generally based upon the detection of a label or marker, such as radioactive, fluorescent, biological and enzymatic tags. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody and/or a biotin/avidin ligand binding arrangement, as is known in the art.

F. Kits

In still further embodiments, the present invention concerns kits for use with the vaccination methods described above. Immunogenic compositions with reduced VLS promoting and/or enzymatic toxic effects may be provided in a kit. Such kits may be used to provide immunogens, vaccine components or vaccine preparations for vaccination in a ready to use and storable container.

The container of the kits will generally include at least one vial, test tube, flask, bottle, syringe and/or other container, into which at least one immunogenic composition, antibody, vaccine component or vaccine may be placed, and/or preferably, suitably aliquoted. The kits of the present invention may include a means for containing vaccine components, vaccines or any other reagent containers in close confinement for commercial sale. Such containers may include injection and/or blow-molded plastic containers into which the desired vials are retained.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Structural Motif for Initiating Vascular Leak Syndrome

This example demonstrates that a three amino acid sequence motif, (x)D(y), in toxins and IL-2 is responsible for damaging vascular ECs. Short (<20 amino acid) (x)D(y) motif-containing peptides from RTA or IL-2 which contained flanking glycine residues and an N-terminal cysteine residue, as well as peptides with deleted or mutated sequences, were generated. These peptides were separately attached via the cysteine residue to a mouse IgG1 Mab (RFB4) not reactive with HUVECs. The VLS-inducing ability of these IgG-peptide conjugates in three VLS model systems were compared. The first model system was in vitro damage to human umbilical endothelial cells, (HUVECs) (Soler-Rodriguez et al., 1993); the second was in vivo fluid accumulation in mouse lungs (Baluna and Vitetta, 1996); and the third was in vivo fluid accumulation in human skin xenografts in SCID mice (Baluna and Vitetta, 1998).

Peptide Synthesis. A peptide representing 13 amino acids (residues 69-81, SEQ ID NO:1) from RTA, with added N- and C-terminal glycine residues to improve solubility (Table 3), was synthesized. The peptides containing the x(D)$_y$ motif were difficult to solubilize even with the additional three flanking glycines on each end of the peptide. For this reason, they were conjugated to a soluble carrier protein. The MAb RFB4 was chosen because the RFB4-dgRTA is a prototypic immunotoxin (IT), and therefore RFB4-peptides should "mimic" ITs. An N-terminal cysteine was added to couple the peptide to the RFB4 MAb. Two RTA control peptides (Table 3) were synthesized. A peptide of 9 amino acids representing residues 15-23 from IL-2 as well as a control peptide (Table 3) was also synthesized. Again, flanking glycines and a cysteine were added. All peptides were synthesized on an Applied Biosystems Model 430A Solid-phase Peptide Synthesizer.

TABLE 3

Peptides from RTA and IL-2[1]

| Origin | Designation | Type | Peptide Sequence |
|---|---|---|---|
| RTA | LDV+ SEQ ID NO: 4 | Native | C G G G S V T L A L D V T N A Y V G G G<br>              69 70 71 72 73 74 75 76 77 78 79 80 81 |
|  | LDV− SEQ ID NO: 5 | Deleted | C G G G S V T L A T N A Y V G G<br>              69 70 71 72 73 77 78 79 80 81 |
|  | GQT+ SEQ ID NO: 6 | Mutant | C G G G S V T L A G Q T T N A Y V G G G<br>              69 70 71 72 73 74 75 76 77 78 |
| IL-2 | LDL+ SEQ ID NO: 7 | Native | C G G G E H L L L D L Q M G G G<br>              15 16 17 18 19 20 21 22 23 |
|  | LDL− SEQ ID NO: 8 | Deleted | C G G G E H L L Q M G G G<br>              15 16 17 18 22 23 |

[1]Each peptide was conjugated to the mouse MAb, RFB4 as described.

Peptides containing the LDV motif of RTA and the LDL motif of IL-2, when attached to the RFB4 MAb specifically bind to and damage HUVECs in vitro. The IgG-peptide conjugates and the IgG-RTA IT were equally effective in inducing endothelial cell damage and increased vascular permeability in all three models.

The LDV sequence in RTA may be responsible for the initiation of events leading to VLS-like symptoms in vivo since injection of RFB4-RTA-peptides containing the native, but not mutated or deleted, LDV sequence caused vascular leak in lungs and in human skin xenografts in a manner analogous to that of the RFB4-dgRTA IT. dgRTA utilizes its LDV sequence, at least in part, to bind to HUVECs since peptides or proteins containing this motif inhibited the dose-dependent, saturable binding of RTA to HUVECs.

The stereoviews of LDV in RTA and LDL in IL-2 indicate that these motifs are partially exposed and should interact with cells. For RTA, this is supported by its dose dependent, saturable binding to HUVECs in vitro. Since the binding of RFB4-LDV+ to HUVECs could be partially inhibited not only by dgRTA but also by proteins containing LDV or LDV-homologues, i.e. Fn and PE38-lys, this further indicates a functional conservation in the (x)D(y) motif in several divergent molecules. Deletions or mutations in this sequence or the use of non-damaging blocking peptides may increase the therapeutic index of both IL-2 as well as ITs prepared with a variety of plant or bacterial toxins.

EXAMPLE 2

Reduced Pulmonary Vascular Leak in Mice

In this example, it was demonstrated that the enzymatic site or the putative VLS-inducing site in RTA can be mutated without effecting the activity of the other site. The results showed that an active site mutant (E177D) induces EC damage and pulmonary vascular leak while one particular LDV mutant (L74A) makes an active IT but does not induce this damage. Thus, a single amino acid change (L74A) yields an RTA with the desirable properties of IT activity with reduced vascular damage. These results demonstrate that it is now possible to generate an effective RTA-containing IT which does not cause VLS.

Plasmids and mutagenesis. It has been shown that E177 in RTA is one of several amino acids involved in the active site and that an E177D mutant has greatly reduced enzymatic activity. The pKK223 plasmid comprises the wt RTA gene and the pUC 18 plasmid comprises the E177D mutant RTA gene, both under IPTG-inducible control (O'Hare et al., 1987; Simpson et al., 1995). In addition, from the (wt)RTA construct, RTA mutants with conserved changes in the LDV sequence were generated. All DNA manipulations were performed using standard techniques (Sambrook et al., 1989). Mutations were introduced into the wt sequence using QuikChange® (Stratagene) and mutagenic primer pairs as shown in Table 4. These mutants included L74A, D75N, D75A, D75E and V76A.

TABLE 4

Mutants and Primers

| Designation | Amino Acid Sequence[1] | Designation | Mutagenic Primer Sequences[2] |
|---|---|---|---|
| Wt<br>SEQ ID NO: 9 | L A L D V T N A Y V V | | |
| L74a<br>SEQ ID NO: 10 | L A A D V T N A Y V V | SEQ ID NO: 15 | CTTTCTGTTACATTAGCCGCGGATGTCACCAATGCATATG |
| D75A<br>SEQ ID NO: 11 | L A L A V T N A Y V V | SEQ ID NO: 16 | GTTACATTAGCCCTGGCTGTCACCAATGCATATG |
| D75E<br>SEQ ID NO: 12 | L A L E V T N A Y V V | SEQ ID NO: 17 | CTGTTACATTAGCCCTGGAAGTCACCAATGCATATG |

TABLE 4-continued

Mutants and Primers

| Designation | Amino Acid Sequence[1] | Designation | Mutagenic Primer Sequences[2] |
|---|---|---|---|
| D75N SEQ ID NO: 13 | L A L <u>N V</u> T N A Y V V | SEQ ID NO: 18 | CTGTTACATTAGCCCTGAACGTCACCAATGCATATGTGG |
| V76A SEQ ID NO: 14 | L A <u>L D</u> A T N A Y V V | SEQ ID NO: 19 | GTTACATTAGCCCTGGATGCTACCAATGCATATGTGGTC |

[1]VLS consensus sequence, LDV, is underlined; the active site residue, Y, is bold
[2]A pair of primers corresponding to both complementary strands of this sequence used in the mutagenesis reaction Expression of RTA in *E. coli*. Overnight cultures of *E. coli* strain XL1-Blue freshly transformed with either plasmid in Terrific Broth (Sambrook et al., 1989) containing 100 µg/mL ampicillin at 37° C. were used to inoculate (1%) 500 mL of the same media (in 2 L flasks). Cultures were grown at 30° C. with vigorous shaking until they had reached an $OD_{600}$ of 0.6 to 0.8. Expression was induced using 0.3 mM IPTG and the cultures allowed to grow overnight (~15 h). Scaled up expression was carried out in a 5 L fermentor (New Brunswick Scientific, Edmon, N.J.) with the same media and inoculum as above. Cultures were grown with agitation of 400 rpm and airflow of 4.0 L/min at 37° C. until $OD_{600}$ of 0.5. The cultures were slowly cooled to 30° C., induced with 1.0 mM IPTG, and grown 16-18 h with agitation of 250 rpm and airflow of 2.5 L/min. Cells were harvested and resuspended in 10 mL PBS (50 mM phosphate-buffered saline, pH 7.0) and lysed by sonication (six 30-second bursts) or by passage through a French Press (Spectronic Instruments). Cell debris was removed by centrifugation at 15K rpm for 20 min; supernatants were filtered (0.2 µm) and stored at −20° C. until purification.

Radioimmunoassay (RIA) and bioassay of expressed RTA. The yield of expressed RTA was assayed using a solid phase RIA. In this assay wells of microtiter plates are coated with an affinity purified rabbit anti-RTA. Plates are washed and blocked with BSA. Dilutions of purified rRTA (standard curve) or of sample are added for 2 hrs at 25° C. Plates are washed and 100,000 cpm of $^{125}$I affinity purified rabbit anti-RTA is added to each well for 1 hr at 25° C. Plates are washed. Wells are cut out and counted on a gamma counter. Concentration of rRTA in the *E. coli* extracts were determined from the standard curve.

Purification of rRTAs. rRTAs were purified from the bacterial lysates by ion-exchange chromatography on CM-Sepharose fast flow (Pharmacia). pH 6-9 proteins were eluted using a 0-300 mM NaCl gradient. Pooled fractions, comprising the main protein peak typically contained 50-80% rRTA. This pool was further purified by chromatography on Blue-Sepharose CL-4B; bound rRTA was eluted with 1 M NaCl (Ghetie et al., 1991). The RTA preparations were concentrated to 3-4 mg/mL and stored at −20° C. in 50% glycerol. Purified RTA preparations were evaluated by sodium dodecyl sulfate polyacrylamide gel electrophoresis (SDS-PAGE) and were >90% pure. The enzymatic activity of wt rRTA, dgRTA and the mutant rRTAs was determined using a cell-free rabbit reticulocyte assay (Press et al., 1988).

Preparation of RFB4-RTA. The murine Mab, RFB4 (anti-human-CD22) was chemically conjugated to rRTAs and dgRTA using N-succinimidyl-oxycarbonyl-α-methyl-α (2-pyridyldithio) toluene (SMPT, Pierce) and purified as described previously for dgRTA (Ghetie et al., 1991; Knowles and Thorpe, 1987). The enzymatic activity of the RTA in the ITs was tested in the cell-free rabbit reticulocyte assay, following reduction (Press et al., 1988).

In vitro cytotoxicity assays. The cytotoxic activities of the different RFB4-containing-ITs were determined using $CD22^+$ Daudi cells and [³H]-leucine incorporation as described previously (Ghetie et al., 1988). The concentration of IT which reduced [³H]-leucine incorporation by 50% relative to an untreated control culture was defined as the $IC_{50}$.

As shown in Table 5, when tested in the reticulocyte assay, the wt RTA and dgRTA had very similar activities although the wt RTA was slightly more active. Following coupling to the RFB4 Mab, dgRTA was approximately 3-fold less toxic than wt RTA. In contrast, the E177D rRTA and the RFB4-E177D IT were 3200 fold and 560 fold less enzymatically activite, respectively, in the reticulocyte assay and greater than $5 \times 10^7$ fold less toxic in the Daudi cell assay (Table 4 and FIG. 3). RFB4-EI77D, which bound to Daudi cells as effectively as RFB4-wtRTA, was virtually inactive as an IT.

TABLE 5

The Enzymatic Activity of rRTAs and ITS prepared with these RrTAs

| RTA | Fold decrease in activity of RTA vs wt RTA | Cell Free Reticulocyte Assay Fold decrease in activity vs wt RFB4-RTA | Daudi Cytotoxicity Assay Fold decrease in activity vs wt RFB4-RTA |
|---|---|---|---|
| Wt | —[a] | —[b] | —[c] |
| DgRTA | 1.3 ± 0.6 (8)[d] | 3.0 ± 1.1 (6) | 4.4 ± 1.6 (19) |
| L74A[e] | 1.5 ± 0.4 (3) | 1.2 ± 0.8 (3) | 9.1 ± 5.3 (4) |
| D75N[e] | 13.5 ± 6.6 (4) | 5.5 ± 1.4 (4) | 660 ± 270 (3) |
| D75A[e] | 3.1 ± 1.7 (3) | 4.0 ± 2.8 (4) | 370 ± 240 (4) |
| D75E[e] | 5.1 ± 2.1 (3) | 12.2 ± 10.3 (5) | 260 ± 200 (5) |
| V76A[e] | (in progress) | 2.7 ± 1.6 (2) | 5.5 ± 3.2 (4) |
| E177D[e] | 3200 ± 1100 (3) | 560 ± 450 (5) | $5.0 \times 10^7$ (8) |

[a]In 16 studies the $IC_{50}$ was $1.4 \pm 0.7 \times 10^{-11}$M
[b]In 18 studies the $IC_{50}$ was $6.4 \pm 1.8 \times 10^{-12}$M
[c]In 18 studies the $IC_{50}$ was $1.6 \pm 0.9 \times 10^{-13}$M
[d]Number of studies using 3 different preparations of each mutant
[e]Refers to the RTA mutation in the LDV sequence or the active site (E177)

Figure 3:
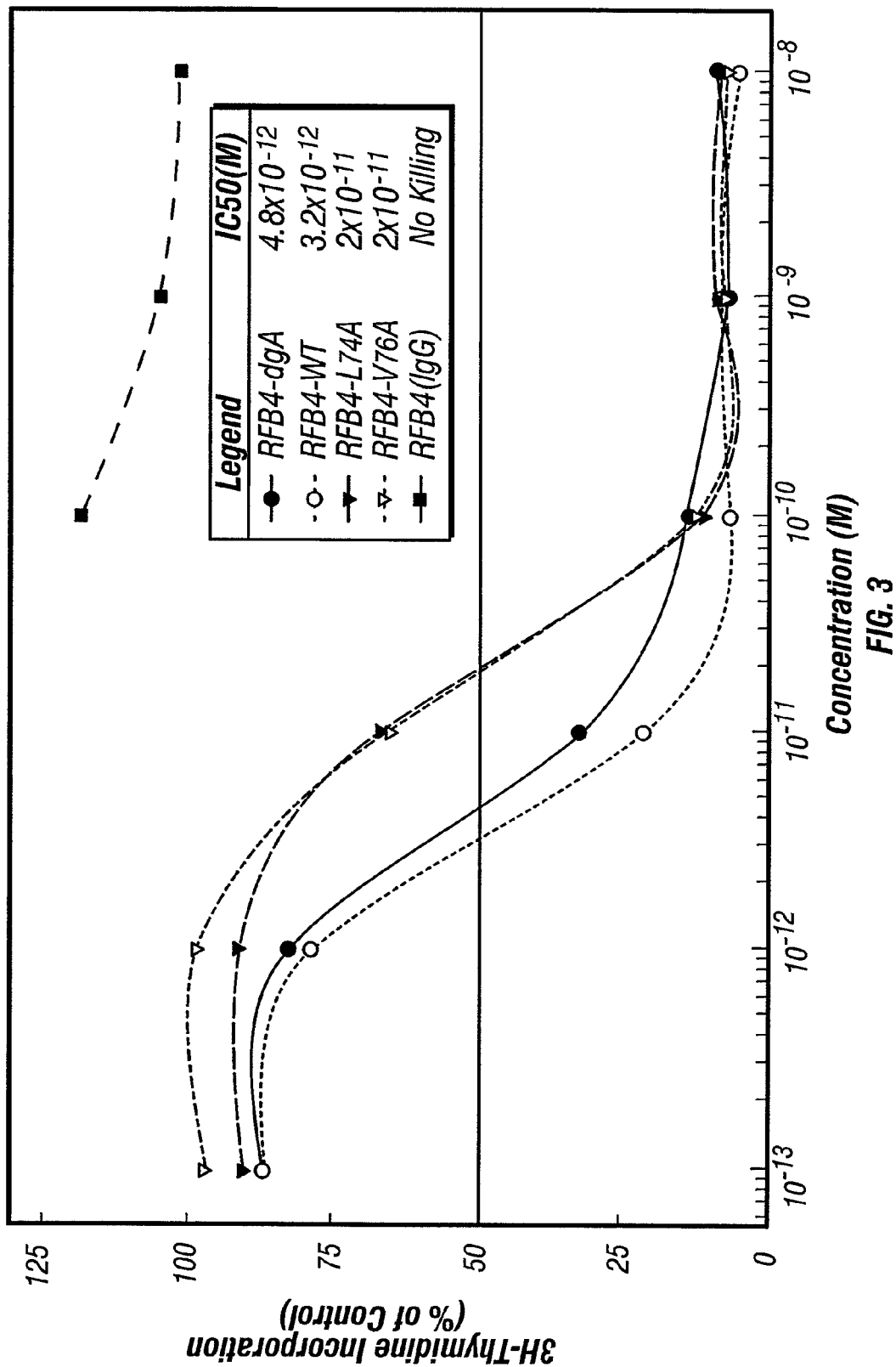
FIG. 3. RFB4-rRTA ITs $IC_{50}$ determinations. Selected examples of $IC_{50}$ determinations by in vitro cytotoxicity assays, where $IC_{50}$ is calculated as the concentration of IT at which [$^3$H]-leucine incorporation was inhibited by 50% relative to untreated control Daudi cell culture.

With regard to the LDV mutants, as compared to wt RTA, L74A was 1.2-1.5 less active in the reticulocyte assay and 6-9-fold less active as an IT in the Daudi cell cytotoxicity assay (Table 5 and FIG. 3). As compared to dgRTA, the L74A IT was 2-fold less active in the Daudi assay. Similar decreases were observed using V76A (Table 5). In contrast to both the L74A and V76A mutants, D75A, D75E and D75N were 3-13-fold less active in the reticulocyte assay, and >200 fold less active as ITs in Daudi cell cytotoxicity assays. This result indicated that D75 may be particularly important for internalization, for routing, or for intracellular stability of the RTA in Daudi cells. As compared to the wtRTA, L74A and V76A formed the most active IT.

Vascular toxicity of RFB4-rRTA. As a first step in evaluating the ability of ITs prepared with mutant RTAs to induce vascular damage, a series of in vitro studies using HUVECs was conducted. For in vitro assays, the effect of RFB4-rRTA on the morphology of HUVECs monolayers was tested as described previously (Baluna et al., 1996).

Figure 4:
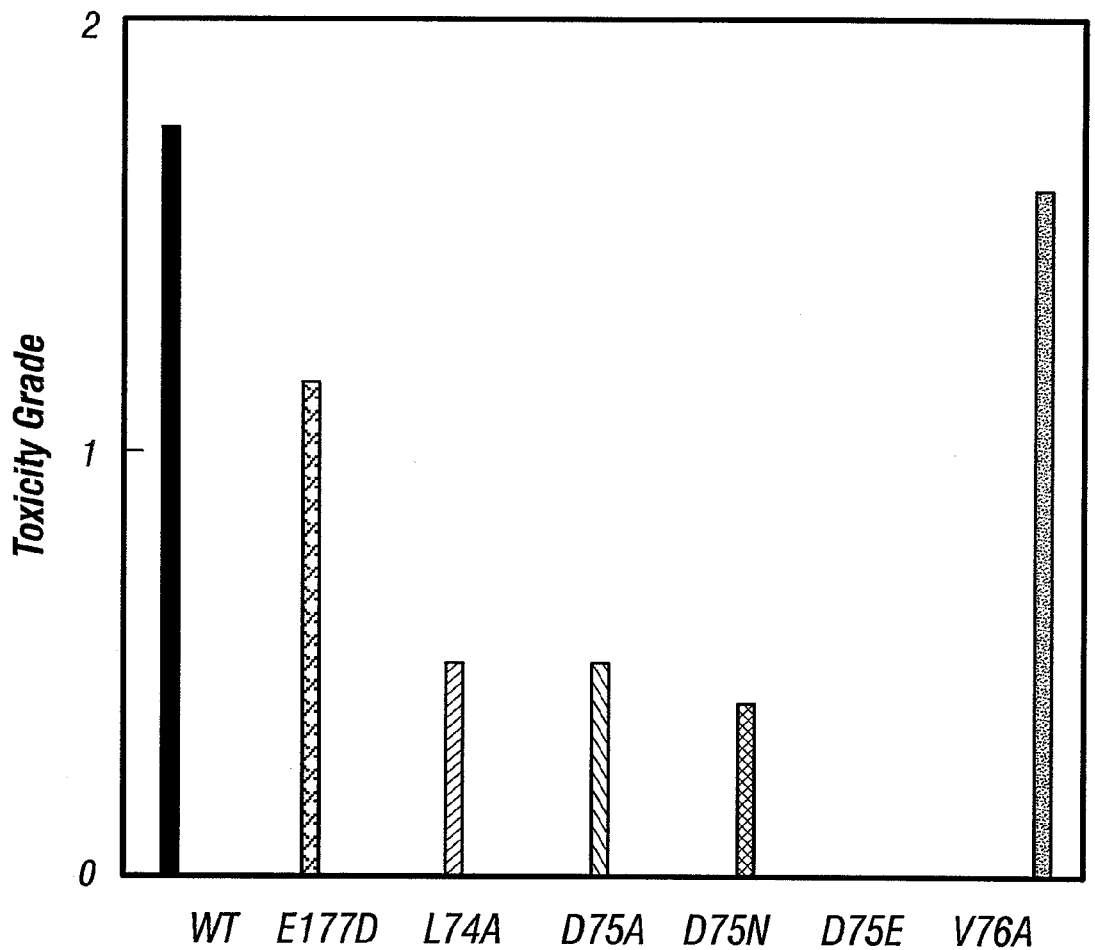
FIG. 4. Effect of RFB4-rRTA ITs on the morphology of HUVEC monolayers. HUVEC monolayers were incubated at 37° C. for 18 h with 100 μg/ml of RFB4-rRTA ITs in M199 medium with 2% fetal calf serum. Morphological changes were scored as: –, no changes; + rounding up of cells; and ++ disruption and detachment of cells from the monolayer. The toxicity grade was represented as a ratio (number of "+"/ number of experiments).

As shown in FIG. 4, the ITs containing wtRTA, dgRTA or the enzymatically inactive E177D RTA damaged HUVECs. Since E177D contains LDV, but has a disrupted active site and is inactive as an IT, this indicated that the active site of RTA and the putative VLS-inducing site (LDV) of RTA are distinct and that enzymatic activity does not appear to be the most important feature for the ability of RTA to damage HUVECs. In contrast, when ITs containing mutations in L, D or V (but not the active enzymatic site) were tested on HUVECs, only the IT containing V76A damaged these cells. Taken together with the results of the Daudi cell studies, the only IT which was active in the Daudi cell cytotoxicity assay and inactive in the HUVEC assay contained the mutation L74A. In contrast, ITs prepared with the D75 mutants had greatly reduced activity in the Daudi cytotoxicity assay even though there were not toxic to HUVECs. Conversely, the IT prepared with E76A was active on Daudi cells, but damaged HUVECs. Of the ITs prepared with the five LDV mutants, the L74A mutant appeared to contain both of the desired properties in vitro.

For in vivo assays, the effect of RFB4 ITs was determined in the SCID/Daudi tumor model (Ghetie et al., 1992). Female SCID mice were injected I.V. (lateral tail vein) with $5 \times 10^6$ Daudi cells on day zero. ITs were injected I.V. on days 1, 2, 3 and 4. Groups of 5 mice were used for each treatment and studies were repeated. Treatment groups received (1) no treatment (control); (2) RFB4-dgRTA 40% of the $LD_{50}$ or 60 μg/mouse; (3) RFB4-wt RTA, 40% of the $LD_{50}$ or 80 μg; (4) RFB4 E177D, 40% of the $LD_{50}$ or 400 μg/mouse; (5) RFB4 L74A, 40% of the $LD_{50}$ or 400 μg/mouse; (6) RFB4 V76A, 40% of the $LD_{50}$ or 400 μg/mouse. Mice were monitored and sacrificed when paralysis of their hind legs occurred. Pulmonary vascular leak in IT-injected SCID mice was evaluated as described (Baluna et al., 1999). The water content of the lungs was calculated as the wet/dry weight ratios of lungs removed from mice injected with 10 μg 1 T/g of mouse weight.

Figure 5B:
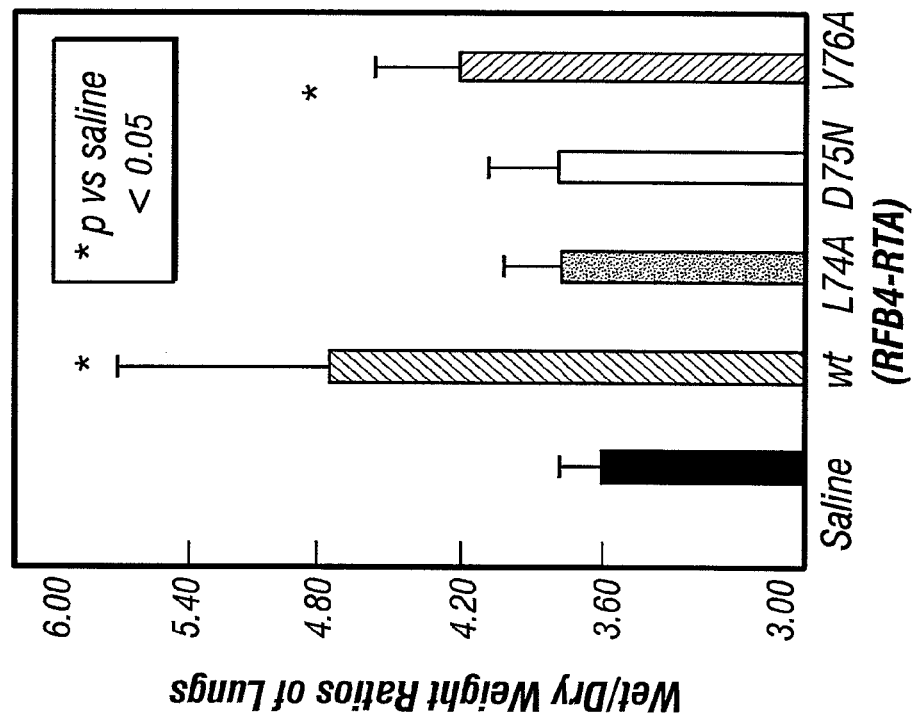
FIGS. 5A and 5B. In vivo effect of RFB4-rRTA ITs. SCID mice were injected with 200 μg of RFB4-rRTA ITs of saline.
Figure 5A:
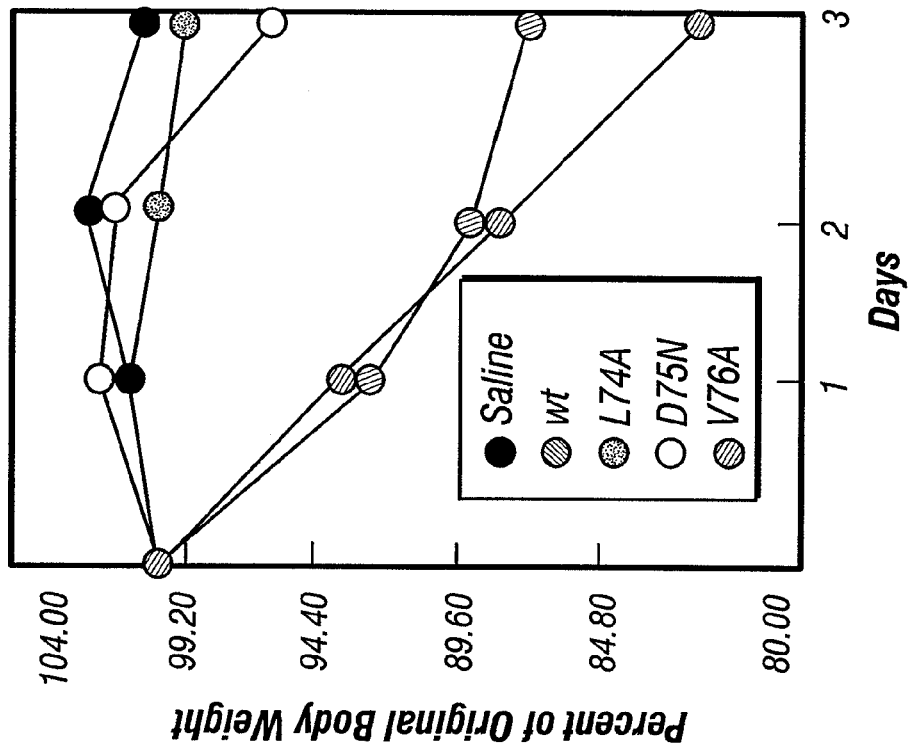
Figure 6:
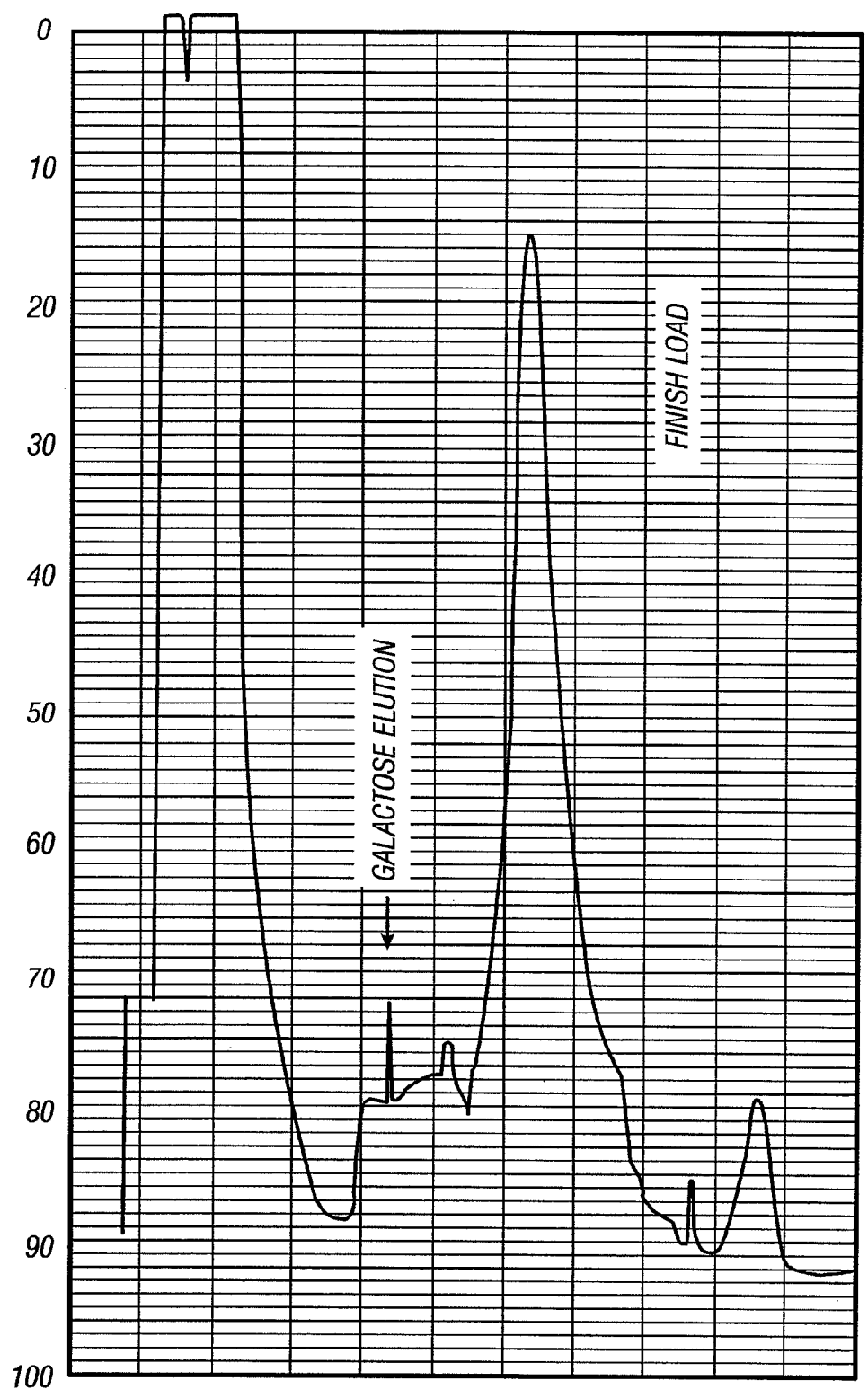
FIG. 6. Profile of Acid-Treated Sepharose 4B Column-Purification of Ricin.
Figure 7:
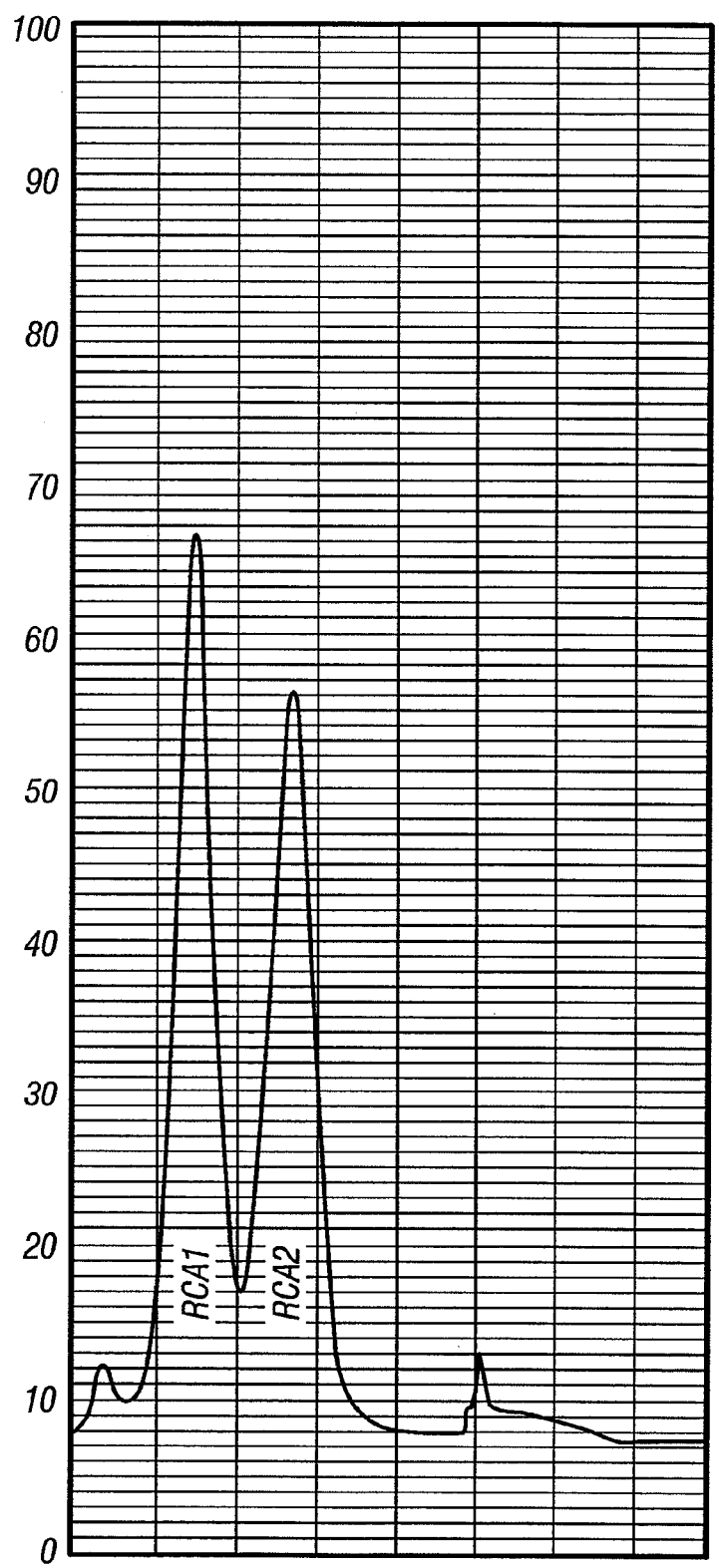
FIG. 7. Profile of Sephacryl S-200 Column-Separation of RCA-1 and RCA-2.
Figure 8:
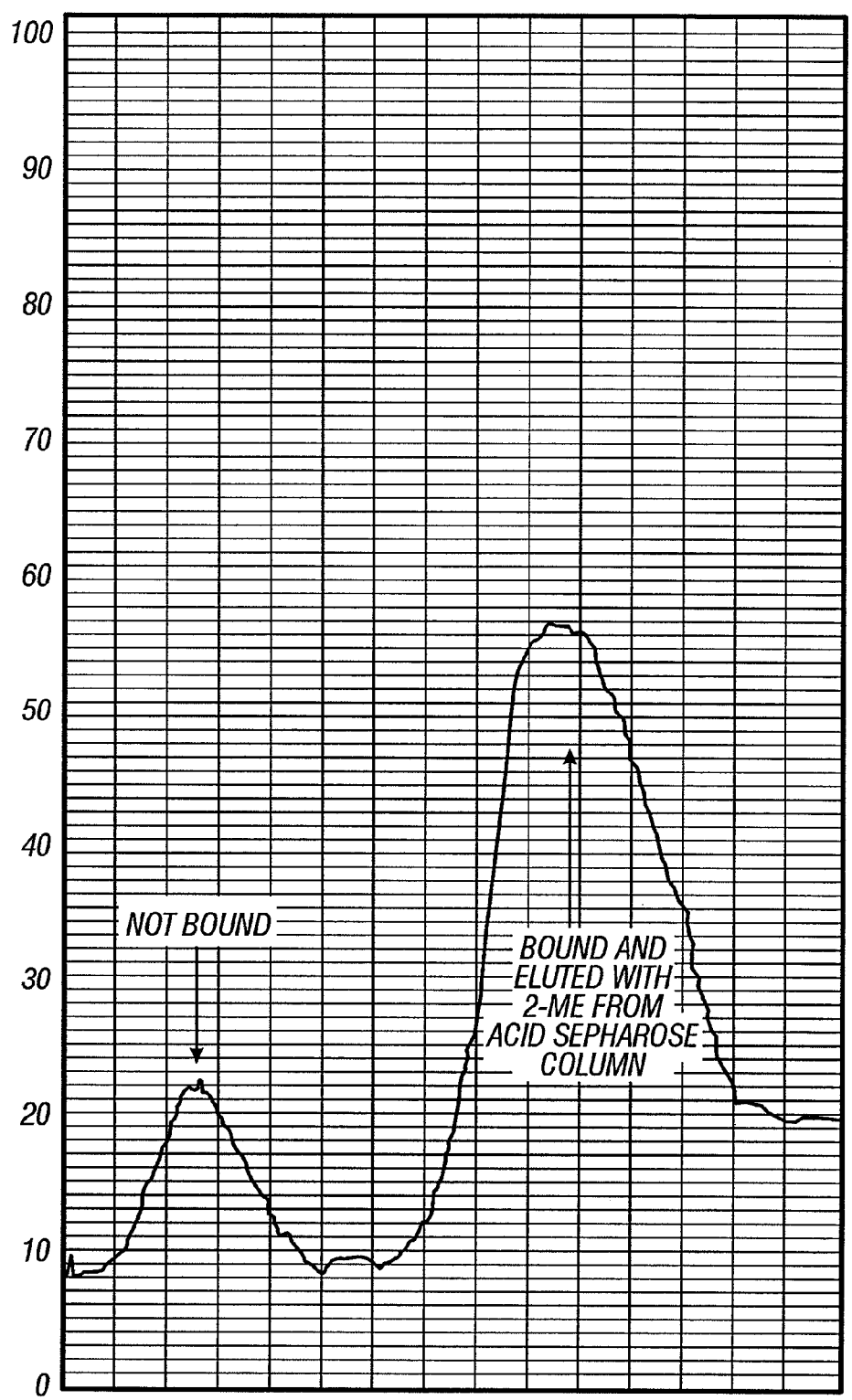
FIG. 8. Profile of DEAE Sepharose Column and Acid-Treated Sepharose 4B Column-Separation of dgRTA and DGRTB Chains.
Figure 9:
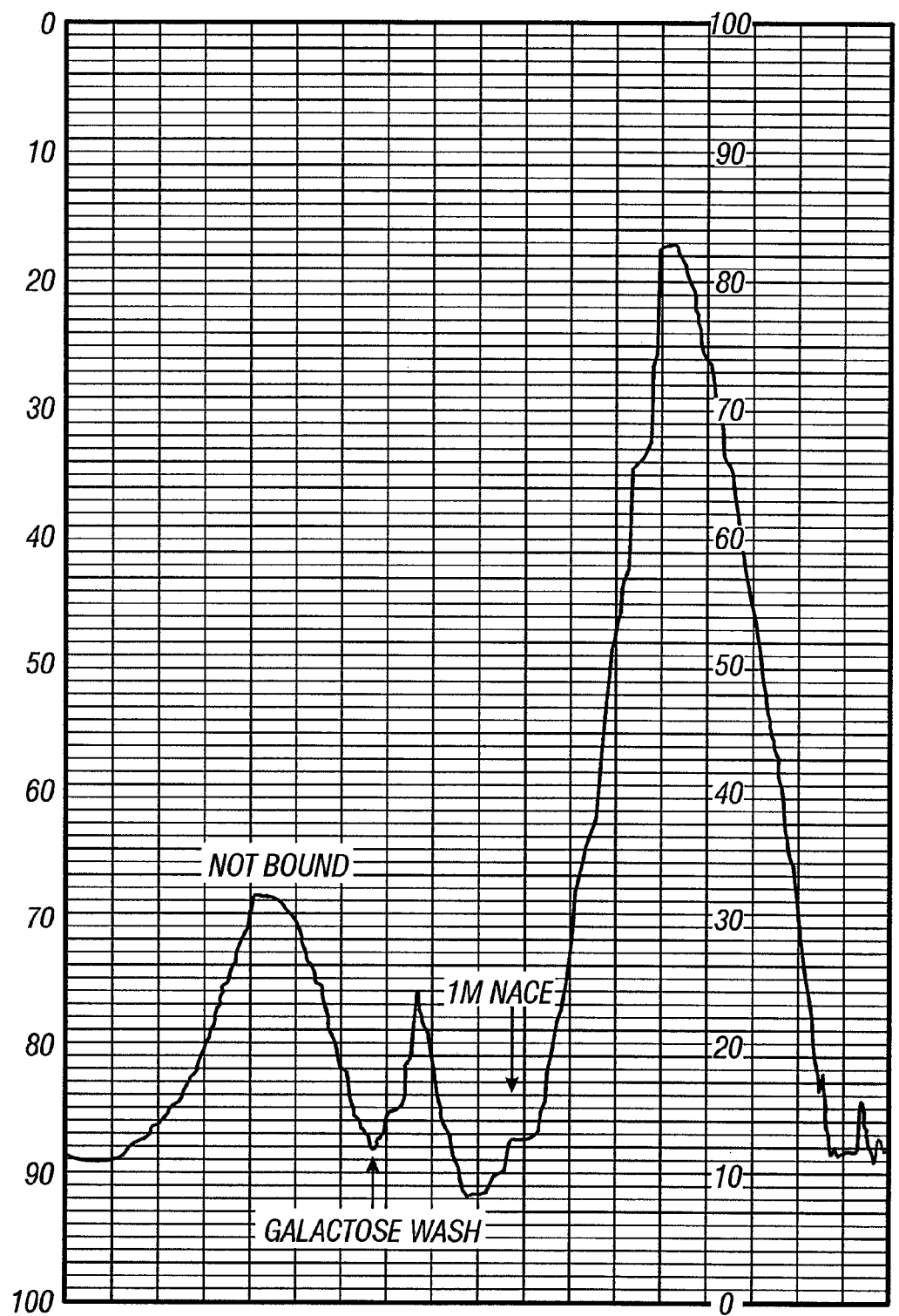
FIG. 9. Profile of Blue-Sepharose CL-4B Column—Purification of dgRTA.
Figure 10:
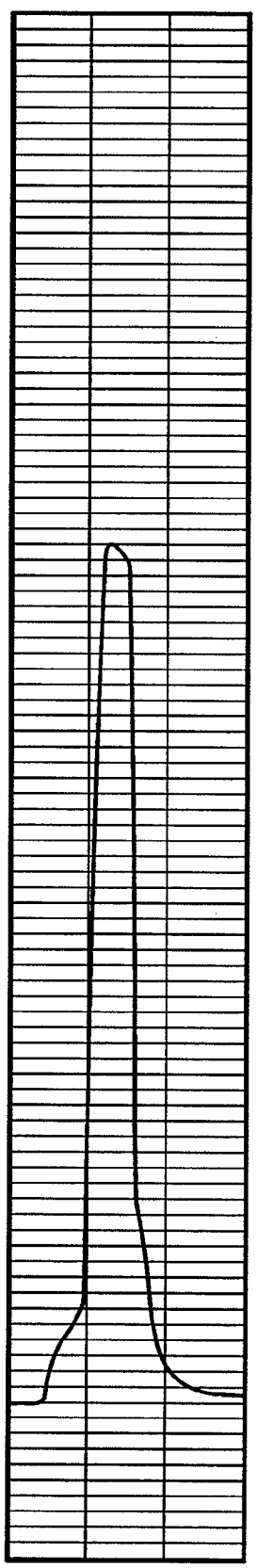
FIG. 10. Profile of Asialofetulin-Sepharose Column—Purification of dgRTA.

Unlike humans, mice injected with RTA-containing ITs do not manifest systemic VLS in terms of weight gain and edema but they do lose significant weight and show pulmonary vascular leak. SCID mice were injected with the ITs prepared with the mutant rRTAs and monitored for both weight loss and pulmonary vascular leak. As shown in FIG. 5, when mice were injected with 10 ug IT/g of body weight, both weight loss (A) and pulmonary leak (B) were observed using the ITs prepared with dgRTA, wtRTA or V76A. In contrast, the ITs containing L74A D75A, D75N or D75E did not induce weight loss or pulmonary leak. At this dose, the RFB4-EI77D IT did not cause weight loss but did induce pulmonary leak. These results further demonstrated that the IT containing L74A RTA possesses the desired properties. It is contemplated that weight loss is related primarily to the LDV sequence but that severe weight loss, as seen in the IT prepared with wt RTA, may be related to both an active site and the LDV sequence of the RTA.

When coupled to RFB4, an active site mutant, E177D, induced EC damage and vascular damage in vivo although RFB4-E177D was $10^7$-fold less active than RFB4-wt RTA in vitro (i.e., it was inactive). A single amino acid change in RTA (L74A) resulted in the expression of a highly active RTA enzyme which made an effective IT both in vitro and in vivo. As compared to RFB4-dgRTA which has been used in mice and patients, RFB4-L74A was only 5-fold less active. At the same dose as RFB4-wt RTA, RFB4-L74A did not damage ECs or cause weight loss in mice. As an IT, it had an $LD_{50}$ which was 20-fold higher than that of an IT prepared with wt RTA, indicating that much higher doses should be safe in vivo. In contrast to RFB4-L74, ITs prepared with mutants containing alterations in D75, although enzymatically active, performed very poorly in the Daudi cytotoxicity assay. Hence D75 may be involved in internalization, intracellular routing or intracellular stability of the RTA. Additionally, a V76 mutant was both enzymatically active and active as an IT but also induced both EC damage and vascular damage.

Taken together, these studies clearly demonstrate that L74A is a desirable RTA mutant. Because RFB4-L74A has a much higher $LD_{50}$ in mice, it will now possible to refine dose regimens to determine whether the therapeutic window has been widened.

EXAMPLE 3

Reticulocyte Assay

To test the ability of dgA (deglycosylated ricin A chain) and dgA derivatives to inhibit protein synthesis in a cell free system.

The following solutions were prepared on a large scale and can be used for multiple assays as long as they are kept sterile.

1 mM hemin was prepared by dissolving 16.3 mg bovine heart hemin and 90 mg KCl in 2.5 ml of 0.2 M Tris, pH 8.2. The solution was brought to 25 ml with ethylene glycol, with the final pH being 8.2. The solution was stored in 100 μl aliquots at −70 C.

0.2 M phosphocreatine was prepared by dissolving 255 mg phosphocreatine in 5 ml double distilled water. The solution was stored in 300 μl aliquots at −20° C.

5 mg/ml creatine phosphokinase, type III bovine heart, was prepared by dissolving the entire contents of a vial by pipetting directly into the vial a mixture of 50% sterile double distilled water and 50% sterile glycerol to a final concentration of 5 mg/ml. The numbers of mg of creatine phosphokinase stated on the purchased vial was used to determine concentration. The solution was stored at 4° C.

50 mM dithiothreitol (DTT) was prepared by dissolving 77.1 mg DTT in 10 ml double distilled water. The solution was stored in 100 μl aliquots at −20° C. protected from light.

Stock salt solution was prepared by dissolving 203 mg $MgCl_2.6H_2O$ (10 mM) and 14.92 gm KCl (2.0 M) in 100 ml double distilled water. The solution was filtered through 150 ml 0.22 μm filter unit. The solution was stored in lower portion of filter unit at 4° C.

Amino acid mixture (minus methionine) was prepared by adding to 80 ml double distilled water: 25.7 mg alanine (3.0 mM); 10.5 mg arginine (0.5 mM); 6.6 mg asparagine (0.5 mM); 7.3 mg glutamine (0.5 mM); 29.4 mg glutamic acid (2.0 mM); 15.0 mg glycine (2.0 mM); 41.9 mg histidine (2.0 mM); 26.6 mg aspartic acid (2.0 mM); 12.0 mg cysteine (0.5 mM); 6.6 mg isoleucine (0.5 mM); 39.6 mg leucine (3.0 mM); 36.5 mg lysine (2.0 mM); 24.8 mg phenylalanine (1.5 mM); 11.5 mg proline (1.0 mM); 21.0 mg serine (3.0 mM); 17.8 mg threonine (1.5 mM); 10.2 mg tryptophan (0.5 mM); 9.0 mg tyrosine (0.5 mM); and 35.1 mg valine (3.0 mM). The solution was mixed thoroughly and adjusted to pH 7.5 with 1 N KOH. 154 mg DTT was added (final 10 mM) and mixed thoroughly. The volume was adjusted to 100 ml. The solution was stored in 300 μl aliquots at −70° C.

The test samples were reduced, if necessary, unless the sample was dgA or A chain alone. Samples of an A chain conjugate (e.g. 1 gG-dgA) was first reduced to dissociate the dgA, by mixing the sample with 1/10 volume 0.1 M Tris HCl, pH 8.0 and 1/10 volume 50 mM dithiothreital. For example, a 1 ml sample was prepared by adding 100 μl Tris-HCl and 100 μl DTT. The sample was incubated for one hour at room temperature protected from light. The molar concentration of immunotoxin was the same as the molar concentration of dgA alone.

Prior to preparing sample dilutions, the stock salt solution, phosphocreatine, amino acid mixture, hemin, creatine phosphokinase and lysate were removed from storage in refrigerator or freezer and placed on ice. Each aliquot was sufficient for two samples of six dilutions each plus 3 control and 3 background wells. One sample was optionally a standard dgA.

Selected dilutions of sample in double distilled water were prepared. A common set may be six serial ten-fold dilutions. These concentrations were diluted 10-fold when the lysate mixture was added. Initial concentrations were prepared accordingly. For example, initial concentrations must be $10^{-7}$M to $10^{-10}$ M for tests from $10^{-8}$M to $10^{-11}$ M. An example of this is as follows:

$$IgG\text{-}dgA \text{ stock concentration} = 0.5 \text{ mg/mL}$$

$$\frac{0.5 \text{ mg/ml}}{180,000} = 2.78 \times 10^{-6} \text{M (molar concentration of stock)}$$

To prepare 1 ml of $1 \times 10^{-7}$M:

$$X(2.78 \times 10^{-6}) = 1 \text{ ml } (1 \times 10^{-7})$$

$X = 36$ μl (volume of stock to add to 964 μl water)

The assay was set up in triplicate in 96-well plate:

5.5 μl of each sample dilution was pipetted in triplicate wells. 6 wells were included with 5.5 μl double distilled water only. Three wells were for the control (maximum level of $^{35}$S-methionine incorporation in the absence of inhibitor) and three wells were for background.

The lysate mixture were prepared using one of the following methods. Each recipe was for one vial of lysate.

Method 1: This method was used for preparations where all reagents will be mixed and added to the plate within 3-5 minutes:

Pipet into a 50 ml centrifuge tube and keep on ice:

| Stock salt solution | 125 μl |
| Phosphocreatine | 125 μl |
| Amino acids mixture | 125 μl |
| Hemin | 40 μl |
| Creatine phosphokinase | 20 μl |
| Lysate | 1 ml |
| Double distilled water | 1 ml |

Mix together gently and immediately pipet 50 μl into each well using a multi-dispense pipettor or multi-channel pipettor and reagent reservoir.

Method 2: This method was used if it took longer than 5 minutes to mix reagents and add the mixture to the plate. Note that protein synthesis began as soon as both solutions are mixed together.

| Solution 1: | |
| --- | --- |
| Hemin: | 40 μl |
| Creatine phosphokinase | 20 μl |
| Lysate | 1 ml |
| Double distilled water | 1 ml |

| Solution 2: | |
| --- | --- |
| Phosphocreatine | 125 μl |
| Amino acids mixture | 125 μl |
| Stock salt solution | 125 μl |

Mix Solution 1 and Solution 2 separately. Just before use, mix two solutions together. Immediately pipet 50 μl into each well using multi-dispense pipettor or multi-channel pipettor and reagent reservoir.

After the lysate mixture was added to wells, it was incubated for 20 minutes at room temperature.

500 μl of double distilled water was pipetted into a vial containing 20 μl $^{35}$S-methionine (0.3 mCi). When the $^{35}$S-methionine is more than three months old, 400 μl or less of water was added.

The plate was pulsed by pipetting 5 μl of $^{35}$S-methionine dilution per well (3 μCi/well) including 3 control wells. The 3 background wells were not labeled at this time. The plates were incubated 40 minutes at room temperature.

Immediately prior to harvesting the plate, 5 μl of $^{35S}$-methionine dilution was pipetted into three background wells. The plates were harvested according to instructions for a plate harvester.

Filter mat discs were placed in scintillation vials and 2-4 ml Cytoscint per vial was added. The vials were capped, and counted in beta counter. The results were calculated by subtracting the mean CPM of background wells from all other counts. Some Beta counters will do this automatically. The percent of maximum incorporation (i.e. percent of control) was calculated as follows:

mean CPM of triplicate sample wells: X 100=% of maximum incorporation mean CPM of triplicate control wells Plot log A chain concentration (M) on the X-axis and percent of maximum incorporation on the Y axis. The $IC_{50}$ is the A chain concentration which yields 50% incorporation.

The cell free reticulocyte assay showed that both active site mutants E177 D and Y80A are 10,000 fold less active than the wild type recombinant A chain.

EXAMPLE 4

Animal Vaccination Improved Survival Against Ricin

Recombinant A (rA) was dialized overnight vs phosphate buffered saline (PBS) to remove the glycerol. The mice were prebled before injecting, and the sera frozen. The hind leg of eight mice were injected intramuscularly with 50 μl rA containing 10 μg protein/mouse (0.2 mg/ml concentration). The weight of each mouse was recorded. For control, the hind leg of ten mice were injected with 50 μl PBS, and the weight of each mouse recorded.

Weekly injections of alternating hind legs were made for total of four injections, and mouse weigh recorded each time.

The immunized mice were bled (25 μl retro-orbitally) in the fifth week one day before challenging with ricin holotoxin. The serum was collected and tested for antibodies against rA. Then, in the fifth week all mice were challenged with 20 ng ricin/g mouse dissolved in 100 μl PBS intraperitoneally, and the weights and any deaths of control and immunized mice daily were noted for ten days. All the vaccinated mice survived.

* * *

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Almendro et al., "Cloning of the human platelet endothelial cell adhesion molecule-1 promoter and its tissue-specific expression. Structural and functional characterization," *J Immunol.* 157(12):5411-5421, 1996.

*Antibodies: A Laboratory Manual*, Cold Spring Harbor Laboratory, Cold Spring Harbor, N.Y., 1988.

Atherton et al., *Biol. of Reproduction*, 32, 155-171, 1985.

Azuma et al., "Correlation between augmented resistance to influenza virus infection and histological changes in lung of mice treated with trehalose-6,6'-dimycolate," *J Biol Response Mod.* 7(5):473-482, 1988.

Baluna and Vitetta, "An in vivo model to study immunotoxin-induced vascular leak in human tissue," *J. Immunother.,* 22(1):41-47, 1999.

Baluna and Vitetta, "Vascular leak syndrome: A side effect of immunotherapy," *Immunopharmacology,* 37:117-132, 1996.

Baluna et al., "Evidence for a structural motif in toxins and interleukin-2 that may be responsible for binding to endothelial cells and initiating vascular leak syndrome," *Proc Natl Acad Sci U S A.*, 96(7):3957-3962, 1999.

Baluna et al., "The effect of a monoclonal antibody coupled to ricin A chain-derived peptides on endothelial cells in vitro: insights into toxin-mediated vascular damage," *Exp Cell Res.* 258(2):417-424, 2000.

Baluna et al., "Fibronectin inhibits the cytotoxic effect of ricin A chain on endothelial cells," *Int. J. Immunopharm.,* 18:355-361, 1996.

Berberian et al., *Science,* 261:1588-1591, 1993.

Blobel and White, "Structure, function and evolutionary relationship of proteins containing a disintegrin domain," *Curr. Opin. Cell Biol.,* 4:760-765, 1992.

Cleary et al., *Trends Microbiol.,* 4:131-136, 1994.

Clements et al., *J. Cell Sci.,* 107:2127-2135, 1994.

Collins et al., *Proc. Natl. Acad. Sci. USA,* 85:7709-7713, 1988.

Coulson et al., *Proc. Natl. Acad. Sci. U.S.A,* 94:5389-5394, 1997.

Cunningham et al., "High-resolution epitope mapping of hGH-receptor interactions by alanine-scanning mutagenesis," *Science* 244(4908):1081-1085, 1989.

De Jager et al., "Current status of cancer immunodetection with radiolabeled human monoclonal antibodies" *Semin Nucl Med* 23(2):165-179, 1993.

Dholakia et al., *J. Biol. Chem.,* 264, 20638-20642, 1989.

Doolittle M H and Ben-Zeev O, "Immunodetection of lipoprotein lipase: antibody production, immunoprecipitation, and western blotting techniques" *Methods Mol Biol.,* 109: 215-237, 1999.

Downie et al., *Am. J. Respir. Cell Molec. Biol.,* 7:58-65, 1992.

Dubos et al., *Am. Rev. Tuber.* 56:334-345, 1947.

Dutcher et al., *J. Clin. Oncol.,* 9:641-648, 1991.

Engert et al., In: *Clinical Applications of Immunotoxins*, Frankel (ed.), 2:13-33, 1997.

Freifelder, *Physical Biochemistry*, Second Edition, pp 238-246.

Gefter et al., *Somatic Cell Genet.* 3:231-236, 1977.

Ghetie et al., "The GLP large scale preparation of immunotoxins containing deglycosylated ricin A chain and a hindered disulfide bond," *J. Immunol. Methods,* 142(2):223-230, 1991.

Ghetie et al., *Cancer Res.* 48:2610, 1988.

Goding, In: *Monoclonal Antibodies: Principles and Practice,* 2d ed., Orlando, Fla., Academic Press, pp. 60-61, 65-66, 71-74, 1986.

Greenspoon et al., *Int. J. Pept. Res.,* 43:417-424, 1994.

Gulbis B and Galand P, "Immunodetection of the p21-ras products in human normal and preneoplastic tissues and solid tumors: a review" *Hum Pathol* 24(12):1271-1285, 1993.

Halling et al., "Genomic cloning and characterization of a ricin gene from *Ricinus communis,*" *Nucleic Acids Res.* 13(22):8019-8033, 1985.

Hewetson et al. *Vaccine,* 11(7):743-748, 1993.

Hewetson et al., "A Formalinized Toxoid for Protection of Mice from Inhaled Ricin", Vaccine Research, vol. 4, No. 4, pp. 179-187, 1995.

Huang, *Cellular and Molecular Life Sciences,* 54:527-540, 1998.

Hunter et al., "Adjuvant activity of non-ionic block copolymers. IV. Effect of molecular weight and formulation on titre and isotype of antibody," *Vaccine.* 9(4):250-256, 1991.

Husain and Bieniarz, *Bioconjug. Chem.,* 5:481-490, 1994.

Husson et al., "Gene replacement and expression of foreign DNA in mycobacteria," *J Bacteriol.* 172(2):519-524, 1990.

Inouye et al., "Up-promoter mutations in the 1 pp gene of *Escherichia coli,*" *Nucl. Acids Res.,* 13:3101-3109, 1985.

Jackson et al., *J. Med. Chem.,* 40:3359-3368, 1997.

Jacobs et al., "Introduction of foreign DNA into mycobacteria using a shuttle phasmid," *Nature,* 327(6122):532-535, 1987.

Kang et al., *Science,* 240:1034-1036, 1988.

Khatoon et al., *Ann. of Neurology,* 26, 210-219, 1989.

King et al., *J. Biol. Chem.,* 269, 10210-10218, 1989.

Knowles, P. P. and Thorpe, P. E. *Anal. Biochem.,* 160:440, 1987.

Kohler and Milstein, "Continuous cultures of fused cells secretaring antibody of predefined specificity," *Nature,* 256: 495-497, 1975.

Kohler et al., *Methods Enzymol.,* 178:3, 1989.

Kraus et al., "Alternative promoter usage and tissue specific expression of the mouse somatostatin receptor 2 gene," *FEBS Lett.,* 428(3):165-170, 1998.

Kreier et al., Infection, Resistance and Immunity, Harper and Row, New York, 1991.

Lamb et al., "Nucleotide sequence of cloned cDNA coding for preproricin," *Eur J Biochem,* 148(2):265-270, 1985.

Lareyre et al., "A 5-kilobase pair promoter fragment of the murine epididymal retinoic acid-binding protein gene drives the tissue-specific, cell-specific, and androgen-regulated expression of a foreign gene in the epididymis of transgenic mice," *J Biol. Chem.,* 274(12):8282-8290, 1999.

Lazarus and McDowell, "Structural and functional aspects of RGD-containing protein antagonists of glycoprotein IIb-IIIa," *Curr. Opin. Cell Biol.,* 4:438-445, 1993.

Lee et al., "Activation of beta3-adrenoceptors by exogenous dopamine to lower glucose uptake into rat adipocytes," *J Auton Nery Syst.* 74(2-3):86-90, 1997.

Lemley et al., Programme and Abstracts, Third Asia-Pacific Congress on Animal, Plant and Microbial Toxins, "Ricin Sub-Unit Vaccination in Mice and Protection from Challenge," p. B15, (Jun. 27-Jul. 1, 1993).

Lenert et al., *Science,* 248:1639-1643, 1990.

Li et al., *Proc. Natl. Acad. Sci. USA,* 92:9308-9312, 1995.

Lotte et al., "BCG complications. Estimates of the risks among vaccinated subjects and statistical analysis of their main characteristics," *Adv Tuberc Res.* 21:107-193, 1984.

Lu et al., *J. Biol. Chem.,* 271:289-294, 1996.

Luelmo F., "BCG vaccination," *Am Rev Respir Dis.* 125(3 Pt 2):70-72, 1982.

Maeda et al., *Biochem. Biophys. Res. Commun.,* 241:595-598, 1997.

Makarem and Humphries, *Biochemical Society Transactions,* 19:380 S-382S, 1991.

Martin et al., "Transposition of an antibiotic resistance element in mycobacteria," *Nature,* 345(6277):739-743, 1990.

McLane et al., *Proc. Soc. Exp. Biol. Med.,* 219:109-119, 1998.

Mlsna et al., *Protein Sci.,* 2:429-435, 1993.

Munishkin and Wool, *J. Biol. Chem.,* 270:30581-30587, 1995.

Nakamura et al., *In: Enzyme Immunoassays: Heterogeneous and Homogeneous Systems, Chapter* 27, 1987.

Nomoto et al., "Cloning and characterization of the alternative promoter regions of the human LIMK2 gene responsible for alternative transcripts with tissue-specific expression," *Gene,* 236(2):259-271, 1999.

Nowlin et al., *J. Biol. Chem.,* 268:20352-20359, 1993.

O'Hare et al., *Febs Lett.,* 216(1):73-78, 1987.

Orucevic and Lala, *J. Immunother.,* 18:210-220, 1995.

O'Shannessy et al., *J. Immun. Meth.,* 99, 153-161, 1987.

Owens and Haley, *J. Biol. Chem.,* 259:14843-14848, 1987.

PCT Patent Application WO 91/16347

Potter and Haley, *Meth. in Enzymol.,* 91, 613-633, 1983.

Press et al., *J. Immun.* 141:4410, 1988.

Puri and Rosenberg, *Cancer Immunol. Immunother.,* 28:267-274, 1989.

Puri et al., *Cancer Res.,* 49:969-976, 1989.

Rabinovich et al., "Vaccine technologies: view to the future," *Science,* 265(5177):1401-1404, 1994.

Remington's Pharmaceutical Sciences, 16th Ed. Mack Publishing Company, 1980.

Remington's Pharmaceutical Sciences, 18th Ed. Mack Printing Company, 1990.

Rippy et al., Soc. Tox. Path., "Immunization with Ricin Toxoid Prevents Death and Reduces Lung Injury", p. 10, (Abstract), 1991.

Rosenberg et al., *N. Engl. J. Med.,* 316:889-897, 1987.

Rosenstein et al., *J. Immunol.,* 137:1735-1742, 1986.

Rosenthal, *Am. Rev. Tuber.* 35:678-684, 1937.

Sambrook et al., *In: Molecular Cloning: A Laboratory Manual, Vol.* 1, Cold Spring Harbor Laboratory Press, Cold Spring Harbor, N.Y., Ch. 7,7,19-17.29, 1989.

Sasso et al., *J. Immunol.,* 142:2778-2783, 1989.

Sausville and Vitetta, *In: Monoclonal Antibody-Based Therapy of Cancer,* Grossbard (ed.), 4:81-89, 1997.

Shorki et al., *J. Immunol.,* 146:936-940, 1991.

Silvermann et al., *J. Clin. Invest.,* 96:417-426, 1995.

Simpson et al., *Eur. J. Biochem.,* 232:458-463, 1995.

Snapper et al., "Lysogeny and transformation in mycobacteria: stable expression of foreign genes," *Proc Natl Acad Sci USA.* 85(18):6987-6991, 1988.

Soler-Rodriguez et al., "Ricin A-chain and ricin A-chain immunotoxins rapidly damage human endothelial cells: implications for vascular leak syndrome," *Exp. Cell Res.,* 206:227-234, 1993.

Soler-Rodriguez et al., *Exp. Cell Res.,* 206:227-234, 1993.

Soler-Rodriguez et al., *Int. J. Immunopharm.,* 14(2):281-291, 1992.

Takada et al., "Molecular and structural requirements of a lipoteichoic acid from *Enterococcus hirae* ATCC 9790 for cytokine-inducing, antitumor, and immunogenic activities," *Infect Immun.* 63(1):57-65, 1995.

Tselepis et al., *J. Biol. Chem.,* 272:21341-21348, 1997.

Tsumaki et al., "Modular arrangement of cartilage- and neural tissue-specific cis-elements in the mouse alpha2(XI) collagen promoter," *J Biol. Chem.* 273(36):22861-22864, 1998.

U.S. Pat. No. 3,791,932
U.S. Pat. No. 3,817,837
U.S. Pat. No. 3,826,364
U.S. Pat. No. 3,850,752
U.S. Pat. No. 3,939,350
U.S. Pat. No. 3,949,064
U.S. Pat. No. 3,996,345
U.S. Pat. No. 4,174,384
U.S. Pat. No. 4,275,149
U.S. Pat. No. 4,277,437
U.S. Pat. No. 4,284,412
U.S. Pat. No. 4,366,241
U.S. Pat. No. 4,435,386
U.S. Pat. No. 4,436,727
U.S. Pat. No. 4,436,728
U.S. Pat. No. 4,472,509
U.S. Pat. No. 4,498,766
U.S. Pat. No. 4,505,899
U.S. Pat. No. 4,505,900
U.S. Pat. No. 4,520,019
U.S. Pat. No. 4,578,770
U.S. Pat. No. 4,579,945
U.S. Pat. No. 4,596,792
U.S. Pat. No. 4,599,230
U.S. Pat. No. 4,599,231
U.S. Pat. No. 4,601,903
U.S. Pat. No. 4,608,251
U.S. Pat. No. 4,661,913
U.S. Pat. No. 4,664,911
U.S. Pat. No. 4,682,195
U.S. Pat. No. 4,683,202
U.S. Pat. No. 4,714,682
U.S. Pat. No. 4,767,206
U.S. Pat. No. 4,774,189
U.S. Pat. No. 4,792,447
U.S. Pat. No. 4,857,451
U.S. Pat. No. 4,866,034
U.S. Pat. No. 4,877,611
U.S. Pat. No. 4,938,948
U.S. Pat. No. 4,950,645
U.S. Pat. No. 4,989,977
U.S. Pat. No. 5,021,236
U.S. Pat. No. 5,045,451
U.S. Pat. No. 5,160,974
U.S. Pat. No. 5,196,066

U.S. Pat. No. 5,478,722
U.S. Pat. No. 5,578,706
U.S. Pat. No. 5,686,072
U.S. Pat. No. 4,578,770
U.S. Pat. No. 4,596,792
U.S. Pat. No. 4,599,230
U.S. Pat. No. 4,599,231
U.S. Pat. No. 4,601,903
U.S. Pat. No. 4,608,251
Vial and Descotes, *Drug Safety,* 7:417-433, 1992.
Vitetta et al., *Immunol. Today,* 14:252-259, 1993.
Wayner and Kovach, *J. Cell Biol.,* 116:489-497, 1992.

Wu et al., "Promoter-dependent tissue-specific expressive nature of imprinting gene, insulin-like growth factor II, in human tissues," *Biochem Biophys Res Commun.* 233(1): 221-226, 1997.
Yamamoto et al., "In vitro Augmentation of Natural Killer Cell Activity and Production of Interferon-α/β and -γ with Deoxyribonucleic Acid Fraction from *Mycobacterium bovis* BCG," *Jpn. J. Cancer Res.,* 79:866-873, 1988.
Yeh et al., *Blood,* 292:3268-3276, 1998.
Yin et al., "Effect of various adjuvants on the antibody response of mice to pneumococcal polysaccharides," *Journal of Biological Response Modifiers,* 8(2):190-205, 1989.
Zhao-Emonet et al., "The equine herpes virus 4 thymidine kinase is a better suicide gene than the human herpes virus 1 thymidine kinase," *Gene Ther.* 6(9):1638-1642, 1999.

What is claimed is:

1. An altered ricin A-chain comprising an amino acid substitution in at least one of L74, D75, and V76; and an amino acid substitution in at least one of Y80, Y123, E177, R180, N209, and W211 of SEQ ID NO: 1 and wherein the altered ricin A-chain has a reduced ability to induce vascular leak syndrome and a reduced catalytic activity relative to the native ricin A-chain.

2. The altered ricin A-chain of claim 1, wherein the altered ricin A chain toxin comprises an amino acid substitution in at least one of L74, D75, and V76; and an amino acid substitution in Y80.

3. The altered ricin A-chain of claim 2, wherein the altered ricin A chain toxin comprises an amino acid substitution in at least one of D75 and V76; and an amino acid substitution in Y80.

4. The altered ricin A-chain of claim 3, wherein the altered ricin A chain toxin comprises an amino acid substitution in V76; and an amino acid substitution in Y80.

5. The altered ricin A-chain of claim 3, wherein the altered ricin A chain toxin comprises an amino acid substitution in D75; and an amino acid substitution in Y80.

6. The altered ricin A-chain of claim 4, wherein the substitution in V76 is V76A and the substitution in Y80 is Y80 A.

7. The altered ricin A-chain of claim 5, wherein the substitution in D75 is D75A and the substitution in Y80 is Y80A.

8. The altered ricin A-chain of claim 4, wherein the substitution in V76 is V76M and the substitution in Y80 is Y80A.

* * * * *

SEQUENCE LISTING

<160> NUMBER OF SEQ ID NOS: 19

<210> SEQ ID NO 1
<211> LENGTH: 267
<212> TYPE: PRT
<213> ORGANISM: Artificial Sequence
<220> FEATURE:
<223> OTHER INFORMATION: Description of Artificial Sequence: Synthetic Peptide

<400> SEQUENCE: 1

```
Met Val Pro Lys Gln Tyr Pro Ile Ile Asn Phe Thr Thr Ala Gly Ala
 1               5                  10                  15

Thr Val Gln Ser Tyr Thr Asn Phe Ile Arg Ala Val Arg Gly Arg Leu
            20                  25                  30

Thr Thr Gly Ala Asp Val Arg His Glu Ile Pro Val Leu Pro Asn Arg
        35                  40                  45

Val Gly Leu Pro Ile Asn Gln Arg Phe Ile Leu Val Glu Leu Ser Asn
    50                  55                  60

His Ala Glu Leu Ser Val Thr Leu Ala Leu Asp Val Thr Asn Ala Tyr
65                  70                  75                  80

Val Val Gly Tyr Arg Ala Gly Asn Ser Ala Tyr Phe Phe His Pro Asp
                85                  90                  95

Asn Gln Glu Asp Ala Glu Ala Ile Thr His Leu Phe Thr Asp Val Gln
            100                 105                 110

Asn Arg Tyr Thr Phe Ala Phe Gly Gly Asn Tyr Asp Arg Leu Glu Gln
        115                 120                 125

Leu Ala Gly Asn Leu Arg Glu Asn Ile Glu Leu Gly Asn Gly Pro Leu
    130                 135                 140

Glu Glu Ala Ile Ser Ala Leu Tyr Tyr Tyr Ser Thr Gly Gly Thr Gln
145                 150                 155                 160

Leu Pro Thr Leu Ala Arg Ser Phe Ile Ile Cys Ile Gln Met Ile Ser
                165                 170                 175

Glu Ala Ala Arg Phe Gln Tyr Ile Glu Gly Glu Met Arg Thr Arg Ile
            180                 185                 190

Arg Tyr Asn Arg Arg Ser Ala Pro Asp Pro Ser Val Ile Thr Leu Glu
        195                 200                 205

Asn Ser Trp Gly Arg Leu Ser Thr Ala Ile Gln Glu Ser Asn Gln Gly
    210                 215                 220

Ala Phe Ala Ser Pro Ile Gln Leu Gln Arg Arg Asn Gly Ser Lys Phe
225                 230                 235                 240

Ser Val Tyr Asp Val Ser Ile Leu Ile Pro Ile Ile Ala Leu Met Val
```

```
                245                 250                 255
Tyr Arg Cys Ala Pro Pro Ser Ser Gln Phe
            260                 265

<210> SEQ ID NO 2
<211> LENGTH: 133
<212> TYPE: PRT
<213> ORGANISM: Homo sapiens

<400> SEQUENCE: 2

Ala Pro Thr Ser Ser Thr Lys Lys Thr Gln Leu Gln Leu Glu His
1               5                   10                  15

Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 3
<211> LENGTH: 251
<212> TYPE: PRT
<213> ORGANISM: Abrus precatorius

<400> SEQUENCE: 3

Glu Asp Arg Pro Ile Lys Phe Ser Thr Glu Gly Ala Thr Ser Gln Ser
1               5                   10                  15

Tyr Lys Gln Phe Ile Glu Ala Leu Arg Glu Arg Leu Arg Gly Gly Leu
            20                  25                  30

Ile His Asp Ile Pro Val Leu Pro Asp Pro Thr Thr Leu Gln Glu Arg
        35                  40                  45

Asn Arg Tyr Ile Thr Val Glu Leu Ser Asn Ser Asp Thr Glu Ser Ile
    50                  55                  60

Glu Val Gly Ile Asp Val Thr Asn Ala Tyr Val Val Ala Tyr Arg Ala
65                  70                  75                  80

Gly Thr Gln Ser Tyr Phe Leu Arg Asp Ala Pro Ser Ser Ala Ser Asp
                85                  90                  95

Tyr Leu Phe Thr Gly Thr Asp Gln His Ser Leu Pro Phe Tyr Gly Thr
            100                 105                 110

Tyr Gly Asp Leu Glu Arg Trp Ala His Gln Ser Arg Gln Gln Ile Pro
        115                 120                 125

Leu Gly Leu Gln Ala Leu Thr His Gly Ile Ser Phe Phe Arg Ser Gly
    130                 135                 140

Gly Asn Asp Asn Glu Glu Lys Ala Arg Thr Leu Ile Val Ile Ile Gln
145                 150                 155                 160

Met Val Ala Ala Ala Arg Phe Arg Tyr Ile Ser Asn Arg Val Arg
                165                 170                 175
```

```
Val Ser Ile Gln Thr Gly Thr Ala Phe Gln Pro Asp Ala Ala Met Ile
            180                 185                 190

Ser Leu Glu Asn Asn Trp Asp Asn Leu Ser Arg Gly Val Gln Glu Ser
        195                 200                 205

Val Gln Asp Thr Phe Pro Asn Gln Val Thr Leu Thr Asn Ile Arg Asn
    210                 215                 220

Glu Pro Val Ile Val Asp Ser Leu Ser His Pro Thr Val Ala Val Leu
225                 230                 235                 240

Ala Leu Met Leu Phe Val Cys Asn Pro Pro Asn
                245                 250

<210> SEQ ID NO 4
<211> LENGTH: 20
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 4

Cys Gly Gly Gly Ser Val Thr Leu Ala Leu Asp Val Thr Asn Ala Tyr
1               5                   10                  15

Val Gly Gly Gly
            20

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 5

Cys Gly Gly Gly Ser Val Thr Leu Ala Thr Asn Ala Tyr Val Gly Gly
1               5                   10                  15

Gly

<210> SEQ ID NO 6
<211> LENGTH: 20
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 6

Cys Gly Gly Gly Ser Val Thr Leu Ala Gly Gln Thr Thr Asn Ala Tyr
1               5                   10                  15

Val Gly Gly Gly
            20

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 7

Cys Gly Gly Gly Glu His Leu Leu Leu Asp Leu Gln Met Gly Gly Gly
1               5                   10                  15
```

```
<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 8

Cys Gly Gly Gly Glu His Leu Leu Gln Met Gly Gly Gly
  1               5                  10

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 9

Leu Ala Leu Asp Val Thr Asn Ala Tyr Val Val
  1               5                  10

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 10

Leu Ala Ala Asp Val Thr Asn Ala Tyr Val Val
  1               5                  10

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 11

Leu Ala Leu Ala Val Thr Asn Ala Tyr Val Val
  1               5                  10

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 12

Leu Ala Leu Glu Val Thr Asn Ala Tyr Val Val
  1               5                  10

<210> SEQ ID NO 13
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      Peptide

<400> SEQUENCE: 13

Leu Ala Leu Asn Val Thr Asn Ala Tyr Val Val
 1               5                  10

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 14

Leu Ala Leu Asp Ala Thr Asn Ala Tyr Val Val
 1               5                  10

<210> SEQ ID NO 15
<211> LENGTH: 34
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 15
gttacattag ccctggctgt caccaatgca tatg                              34

<210> SEQ ID NO 16
<211> LENGTH: 36
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 16
ctgttacatt agccctggaa gtcaccaatg catatg                            36

<210> SEQ ID NO 17
<211> LENGTH: 40
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 17
ctttctgtta cattagccgc ggatgtcacc aatgcatatg                        40

<210> SEQ ID NO 18
<211> LENGTH: 39
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 18
ctgttacatt agccctgaac gtcaccaatg catatgtgg                         39
```

```
<210> SEQ ID NO 19
<211> LENGTH: 39
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 19
gttacattag ccctggatgc taccaatgca tatgtggtc                            39
```